US009463275B2

(12) United States Patent
Ueda et al.

(10) Patent No.: US 9,463,275 B2
(45) Date of Patent: Oct. 11, 2016

(54) INFUSION PUMP

(75) Inventors: Mitsutaka Ueda, Osaka (JP); Ryoichi Akai, Osaka (JP); Hidenori Takahashi, Osaka (JP)

(73) Assignee: NIPRO CORPORATION, Osaka (JP)

( * ) Notice: Subject to any disclaimer, the term of this patent is extended or adjusted under 35 U.S.C. 154(b) by 46 days.

(21) Appl. No.: 14/346,828

(22) PCT Filed: Sep. 11, 2012

(86) PCT No.: PCT/JP2012/073145
§ 371 (c)(1),
(2), (4) Date: May 2, 2014

(87) PCT Pub. No.: WO2013/047185
PCT Pub. Date: Apr. 4, 2013

(65) Prior Publication Data
US 2014/0243745 A1    Aug. 28, 2014

(30) Foreign Application Priority Data
Sep. 26, 2011  (JP) .................................. 2011-209735

(51) Int. Cl.
*A61M 1/00*    (2006.01)
*A61M 5/168*   (2006.01)
(Continued)

(52) U.S. Cl.
CPC ..... *A61M 5/16813* (2013.01); *A61M 5/14212* (2013.01); *A61M 5/14228* (2013.01); *F04B 43/082* (2013.01); *A61M 5/14224* (2013.01)

(58) Field of Classification Search
CPC .................... A61M 5/16813; A61M 5/14212; A61M 5/14228; A61M 5/14224; F04B 43/083; F04B 43/14; F04B 43/08; F04B 43/082; F04B 43/12; F04B 43/1223

USPC .......................................... 604/151; 417/474
See application file for complete search history.

(56) References Cited

U.S. PATENT DOCUMENTS

| 5,151,019 A  * |  9/1992 | Danby et al. ................. 417/474 |
| 5,980,490 A  * | 11/1999 | Tsoukalis .................... 604/151 |
| 2011/0158823 A1 |  6/2011 | Wang et al. |

FOREIGN PATENT DOCUMENTS

| CN | 1202577   | 12/1998 |
| DE | 2 820 281 | 11/1979 |

(Continued)

OTHER PUBLICATIONS

International Search Report issued Dec. 18, 2012 in International (PCT) Application No. PCT/JP2012/073145 with English translation.

*Primary Examiner* — Edelmira Bosques
*Assistant Examiner* — Leah Swanson
(74) *Attorney, Agent, or Firm* — Wenderoth, Lind & Ponack, L.L.P.

(57) ABSTRACT

An infusion pump has a primary finger with an inclined surface, which is obliquely inclined to an advancing and retracting direction, and a secondary finger with an inclined surface, which is slidable relative to the inclined surface of the primary finger. When the primary finger is advanced, the secondary finger is retracted in proportion to the variation (increasing) in an entire width of an infusion tube, and when the primary finger is retracted, the secondary finger is advanced in proportion the variation (decreasing) in the entire width of the infusion tube. This configuration can suppress the occurrence of any gap between a tip surface of the secondary finger and an outer peripheral surface of the infusion tube in the advancing and retracting process of the primary finger. Consequently, this prevents the infusion tube from meandering, and suppresses the reduction in the accuracy of the rate of infusion.

10 Claims, 25 Drawing Sheets

(51) Int. Cl.
*A61M 5/142* (2006.01)
*F04B 43/08* (2006.01)

(56) References Cited

FOREIGN PATENT DOCUMENTS

| | | |
|---|---|---|
| GB | 2 020 735 | 11/1979 |
| JP | 55-5485 | 1/1980 |
| JP | 58-74881 | 5/1983 |
| JP | 02-57778 | 2/1990 |
| JP | 02-119690 | 5/1990 |
| JP | 02-124284 | 10/1990 |
| JP | 03-217673 | 9/1991 |
| JP | 3595136 | 12/2004 |
| JP | 2007-023803 | 2/2007 |
| JP | 2009-267349 | 11/2009 |
| JP | 2013-516234 | 5/2013 |
| WO | 99/53201 | 10/1999 |
| WO | 2011/082135 | 7/2011 |

\* cited by examiner (A) retracting process (B) most retracted position (A)

(B)

(A) most retracted position (B) pressing process (C) most advanced position (A) retracting process (B) most retracted position (A)

(B)

(A)

(B)

(A) retracting process (B) most retracted position

INFUSION PUMP

TECHNICAL FIELD

The present invention relates to an infusion pump used such as in the case of infusing an amount of drug solution for medical use into a human body.

BACKGROUND ART

Examples of the infusion pump include a finger-type (peristaltic) infusion pump. The finger-type infusion pump is of the type that sends an amount of infusion solution by driving the infusion tube, which is positioned between a plurality of fingers and a tube pressing plate (pressing plate), to advance and retract and then compressing the infusion tube sequentially with each finger, which is also referred to as a "full-press type". It is problematic that in such full-press type infusion pumps, any settling (flat deformation) of the infusion tube may be occurred, resulting in the reduction in the rate of infusion per unit time.

As a solution for reducing the settling of the infusion tube, a midpress-type (half-occlusion type) infusion pump is proposed (see Patent Document 1, for example). In the infusion pump described in the Patent Document 1, the settling of the infusion tube is reduced by providing a plurality of fingers each of which can be drive the fingers individually in a pump mechanism, pressing the infusion tube in a manner that only the upstream and downstream sides of the infusion tube are fully collapsed while the intermediate portion of the infusion tube between the upstream and downstream sides is not fully collapsed, i.e., it is halfway collapsed. According to this half-occlusion type infusion pump, although the reduction in the rate of infusion can be improved, it is not possible to completely eliminate the reduction of the rate of infusion.

As a technique of forcedly restoring the settling of the tube or the like, there is a tube restoring technique comprising a primary finger which presses a tube and a secondary finger which is moved in a direction orthogonal to a pressing direction for the primary finger, wherein the tube is restored by the secondary finger (see Patent Document 2, for example). In such techniques, as the method of driving the secondary finger, there is a method wherein the secondary finger is connected to the primary finger via a link mechanism and the secondary finger is driven in conjunction with the driving of the primary finger. In addition, as the other driving method, there are the method wherein the primary finger and the secondary finger are driven individually, the method wherein each of the primary and secondary fingers is cam-driven and two cam shafts are connected via a timing belt to drive the primary finger and the secondary finger, and the like.

CITATION LIST

Patent Document

Patent Document 1: Japanese Patent No. 3595136
Patent Document 2: Japanese Patent Laid-Open No. H02-119690
Patent Document 3: Japanese Patent Laid-Open No. S55-005485

SUMMARY OF THE INVENTION

Problems to be Solved by the Invention

However, in the infusion pump with the primary finger and the secondary finger, it is difficult to achieve a linear relationship between the movement of the primary finger and the movement of the secondary finger by the method wherein the secondary finger is driven to the primary finger via a link mechanism, and it is impossible to move the secondary finger in conjunction with the deformation of the infusion tube in an advancing and retracting process of the primary finger. As a result, since the occurrence of any gap between a tip of the secondary finger and an outer peripheral surface of the infusion tube cannot be avoided in the advancing and retracting process of the primary finger, the infusion tube may meander between the tip of the primary finger and the tube pressing plate (meander in an infusion delivery direction). In this case, the accuracy of the rate of infusion would be reduced.

Also in the method of driving individually the primary and secondary fingers and the method of driving each of the primary and secondary fingers by the respective cam shaft, as described above, the phase shift between the movement of the primary finger and the movement of the secondary finger may occur, and therefore it may be problematic to reduce the accuracy of the rate of infusion due to the meandering of the infusion tube as described above. Moreover, these methods problematically may be expensive because one driving system for each of the primary and secondary fingers, totally two systems are required.

The present invention has been made in consideration of these practical problems and intends to provide an infusion pump which can control the reduction in the accuracy of the rate of infusion.

Means for Solving the Problems

The present invention involves an infusion pump comprising a pump mechanism which presses an infusion tube to deliver an amount of infusion solution within the infusion tube, wherein the pump mechanism comprises a primary finger capable of being advanced and retracted relative to the infusion tube, the primary finger pressing the infusion tube when the primary finger is advanced, driving means which advance and retract the primary finger, and a secondary finger capable of being advanced and retracted only in one direction orthogonal to a advancing and retracting direction of the primary finger. Further, the technical feature is in that the present infusion pump is configured so that the primary finger has an inclined surface which is obliquely inclined to the advancing and retracting direction, while the secondary finger has an inclined surface which is slidable relative to the inclined surface of the primary finger and moves the secondary finger in the orthogonal direction through sliding relative to the inclined surface of the primary finger, thereby when the primary finger is advanced and retracted, the inclined surface of the primary finger and the inclined surface of the secondary finger slide relative to each other and the secondary finger is moved in the orthogonal direction in conjunction with the movement of the primary finger.

The action of the present invention will be described below.

Firstly, as shown in FIG. 24(1), assuming that an outer diameter (diameter) of the infusion tube T in a perfect circle is designated as "d", its circumferential length is expressed as "dπ". On the other hand, assuming that the amount of compression of the infusion tube T when the infusion tube T is compressed as shown in FIG. 24(B) is designated as "Δd", an arc length of the infusion tube T is expressed as [(d−Δd)π], the straight portion length of the infusion tube T: W1 is expressed as $$W1=[d\pi-(d-\Delta d)\pi]/2=\Delta d\pi/2.$$

The entire width of the infusion tube T: W2 is expressed as $$W2 = \Delta d\pi/2 + (d - \Delta d) \quad (1)$$
$$= (\pi/2 - 1)\Delta d + d.$$

As apparent from the formula (1), the entire width W2 of the infusion tube T is proportional to the amount of compression Δd (assuming that the circumferential length of the infusion tube is not varied). That is to say, there is the proportional relationship between the position where the primary finger is moved to its most retracted position (amount of compression) and the entire width of the infusion tube T deformed by the primary finger (width of a part where the tips of the secondary finger are coupled).

Focusing on this point, in the present invention, the secondary finger is adapted to be advanced and retracted in conjunction with the variation of the entire width of the infusion tube deformed due to advancing and retracting the primary finger.

In particular, the primary finger has an inclined surface which is obliquely inclined to the advancing and retracting direction (an inclined surface with the inclined angle in consideration of the relationship of the formula (1)), while the secondary finger has an inclined surface which is slidable relative to the inclined surface of the primary finger. Further, the infusion pump according to the present invention is configured so that when the primary finger is advanced, the secondary finger is retracted in proportion to the variation (increasing) in the entire width of the infusion tube, while when the primary finger is retracted, the secondary finger is advanced in proportion the variation (decreasing) in the entire width of the infusion tube. Since this configuration can suppress the occurrence of any gap between a tip of the secondary finger and an outer peripheral surface of the infusion tube in the advancing and retracting process of the primary finger, the meandering of the infusion tube between the tip of the primary finger and the tube pressing plate can be prevented. This can improve the accuracy of the rate of infusion.

Moreover, since the sliding of the primary finger and the secondary finger (the sliding of their inclined surfaces) causes the secondary finger to move, only one driving system is required for the fingers (only one system is required for the primary finger) and the reduction in cost can be contemplated. Also, it is advantageously in that the phase shift between the movement of the primary finger and the movement of the secondary finger is not likely to occur comparing to the conventional driving method described above, i.e., the method of driving individually the primary and secondary fingers or the method of driving each of the primary and secondary fingers by the respective cam shaft.

In the present invention, it is preferable to configured that when the primary finger is in its most retracted position, the tip of the primary finger is placed in the position corresponding to the outer peripheral surface of the infusion tube, and the tip of the secondary finger is placed in the position corresponding to the outer peripheral surface of the infusion tube.

In the present invention, a single secondary finger may be provided for the primary finger. Also two secondary fingers may be provided for the primary finger. In this case, a pair of tapered inclined surfaces opposingly inclined to the advancing and retracting direction is provided on the primary finger and a pair of secondary fingers with an inclined surface slidable relative to each of the inclined surface of the primary finger is provided.

In the present invention, the infusion pump comprises a resilient member which presses the inclined surface of the secondary finger against the inclined surface of the primary finger, and the inclined surface of the primary finger and the inclined surface of the secondary finger may be configured to slide relative to each other because an inclined surface of the secondary finger is pressed by an inclined surface of the primary finger due to the resilient force of the resilient member (for example, compression coil springs) when the primary finger is retracted.

Further, the infusion pump comprises connecting means which slidably connects the primary finger and the secondary finger, and the inclined surface of the primary finger and the inclined surface of the secondary finger may be configured to slide relative to each other due to the connection of the connecting means when the primary finger is retracted. In this case, examples of the connecting means may include a mechanism in which a T-shaped groove and a T-shaped slider are combined and a mechanism in which a trapezoidal-shaped groove and a trapezoidal-shaped slider are combined.

A particular configuration of the present invention may involve a configuration in which valve fingers for occluding openably/closably the infusion tube are provided on each of the upstream and downstream sides of the infusion delivery direction of the primary finger (for example, a half-occlusion type pump mechanism). In this case, a single primary finger may be provided between the upstream side valve finger and the downstream side valve finger, or otherwise a plurality of primary fingers may be provided between them. If the plurality of primary fingers is provided between the upstream side valve finger and the downstream side valve finger, it allows to reduce the pulsation which may be occur in delivering the infusion solution.

Another particular configuration may involve a configuration in which the pump mechanism comprises a plurality of primary fingers capable of being advanced and retracted relative to the infusion tube, the plurality of primary fingers pressing the infusion tube when the plurality of primary fingers is advanced, and driving means which moves individually the plurality of primary fingers in the advancing and retracting direction, the amount of infusion solution being sent out in a peristaltic motion by driving each of the primary fingers to advance and retract to the infusion tube, wherein the secondary finger is provided for each of the primary fingers of the pump mechanism (for example, a full-press type pump mechanism).

Advantageous Effects of Invention

According to the present invention, in the infusion pump comprising the primary finger and the secondary finger, since the primary finger has an inclined surface which is obliquely inclined to the advancing and retracting direction, while the secondary finger has an inclined surface which is slidable relative to the inclined surface of the primary finger, the secondary finger is moved in conjunction with the variation of the entire width of the infusion tube. This can suppress the reduction in the accuracy of the rate of infusion due to the meandering of the infusion tube.

DESCRIPTION OF THE EMBODIMENTS

Figure 1:
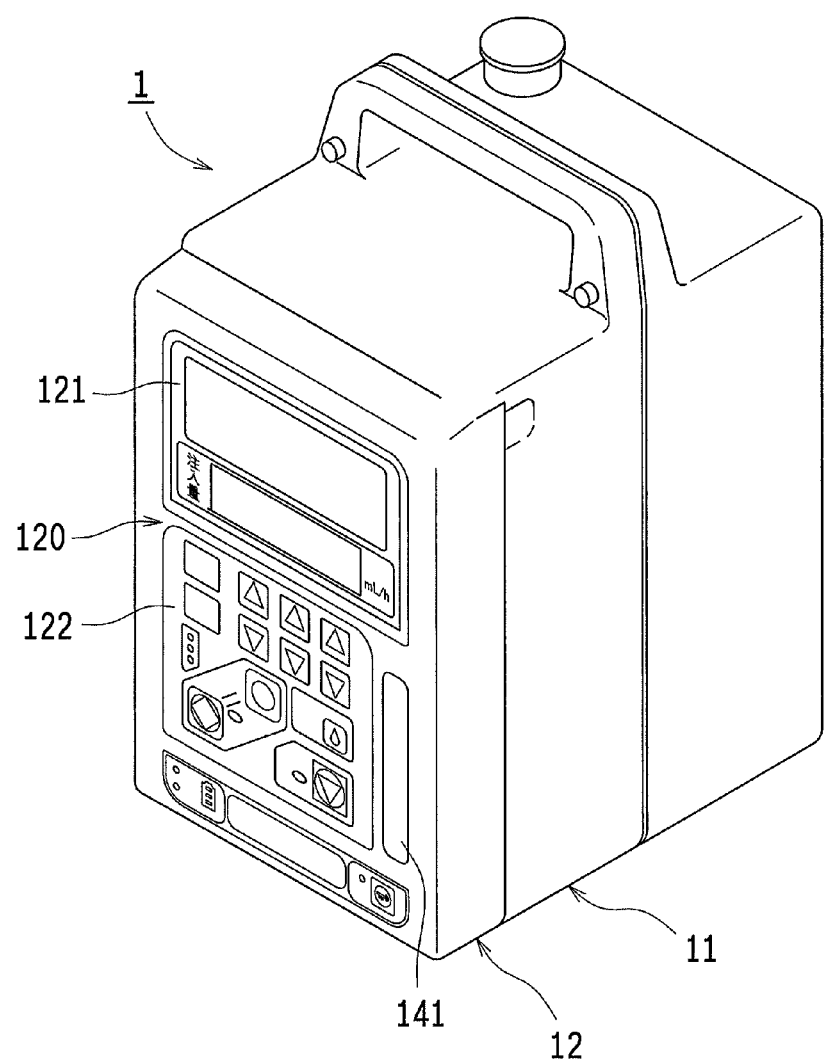
FIG. 1 An appearance perspective view illustrating an example of an infusion pump according to the present invention.

Now, embodiments of the present invention will described below with reference to the drawings.

Embodiment 1

Referring to FIGS. 1-10, an infusion pump according to the present invention will be described.

An infusion pump 1 in this embodiment, which is a half-occlusion type infusion pump, comprises a pump body (casing) 11 and a door 12 which closes a front side (at a tube mounting position) of the pump body 11. The door 12 is swingably (turnably) supported on the pump body 11 by hinges 13, 13 and is adapted to be able to swing from a position to fully close the front side of the pump body 11 to its full open position (for example, a position where the door is opened at 180 degrees).

The pump body 11 and the door 12 have a door lock mechanism 14 to hold the closed state when the door 12 is closed. The door lock mechanism 14 comprises a door lock lever 141, a hook 142 and the like, and therefore the door 12 can be locked by pivoting the door lock lever 141 when the door 12 is closed and then engaging the door lock lever 141 with the hook 142.

The pump body 11 also has a tube mounting guide (guide groove) 111. The tube mounting guide 111 includes, in the order from an upstream side in the infusion delivery direction, an upstream side guide portion 111a, a pump portion 111b extending rectangularly from the upstream side guide portion 111a and a downstream side guide portion 111c. An upstream side valve finger 31, a primary finger 21, a pair of secondary fingers 23, 23, and a downstream side valve finger 41 of the pump mechanism 2 as described below are arranged internally adjacent to the pump portion 111b. Note that on a front wall 110 of the pump body 11, an opening 110a is provided at a position corresponding to the primary finger 21 and the pair of secondary fingers 23, 23 and openings 110b, 110c are provided in the respective positions corresponding to the upstream side valve finger 31 and the downstream side valve finger 41.

The upstream side guide portion 111a of the tube mounting guide 111 is formed into have a laterally curved shape (bent shape). Moreover, the downstream side guide portion 111c on the downstream side of the pump portion 111b is formed into a shape extending linearly in the vertical direction. The groove width of the upstream side guide portion 111a and that of the downstream side guide portion 111c on the downstream side respectively have their dimensions corresponding to the outer diameter of the infusion tubes T (made of polyvinyl chloride or polybutadiene, for example) connected to a drug solution bag, and therefore the infusion tubes T can be mounted into the infusion pump 1 by fitting the infusion tubes T into the upstream side guide portion 111a and the downstream side guide portion 111c.

A tube clamp 112 is provided on the upstream side guide portion 111a. The tube clamp 112 is a member to hold the infusion tube T temporally when mounting the tube on the infusion pump 1 and is adapted to unlock the clamping of the tube automatically when the door 12 is closed after mounting the tube. Note that a clamp lever (not shown) is provided in the vicinity of the tube clamp 112 and the tube clamp 112 can be in an open state by manipulating the clamp lever while mounting the infusion tube T.

A tube pressing plate 6 is provided on the interior side of the door 12. The tube pressing plate 6 is provided in a position corresponding to the pump mechanism 2 (the upstream side valve finger 31, the primary finger 21, the downstream side valve finger 41, etc.). The tube pressing plate 6 is adapted to be opposed to the tips of the primary finger 21 and each of the valve fingers 31, 41 in their most retracted positions with a gap corresponding to the outer diameter of the infusion tube T in the state in which the door 12 is closed. Note that the tube pressing plate 6 is held on a base plate 62 via a buffer sheet 61 (see FIG. 4 etc., for example).

When the infusion tube T is set to the infusion pump 1 configured as above, the door 12 is opened and the infusion tube T connected to the drug solution bag is sequentially fitted into [the upstream side guide portion 111a]→[the tube clamp 112]→[the pump portion 111b]→[the downstream side guide portion 111c], thereby mounting the infusion tube T. After the tube is mounted as mentioned above, the door 12 is closed and locked in the closed state with the door lock mechanism 14, thereby completing the setting of the infusion tube T. Note that, in this example, the tube clamp 112 of the upstream side guide portion 111a is released in the state in which the door 12 is closed, as described above. In addition, when the door 12 is opened such as after infusing is completed, the infusion tube T is occluded by the tube clamp 112 and any free flow in which the infusion falls freely is prevented.

—Pump Mechanism—

Now, a specific example of the pump mechanism 2 will be described with reference to FIGS. 3-6.

The pump mechanism 2 includes a tube pressing section 20, an upstream side valve section 30 and a downstream side valve section 40.

A tube pressing section 20 comprises the primary finger 21, an actuator 22, and a pair of secondary fingers 23, 23 as well as a pair of sliding support members 24, 24 and a pair of compression coil springs 25, 25 on its right and left sides, etc.

The primary finger 21 is a member with a rectangular cross section and has a pair of inclined surfaces 21a, 21a provided on its right and left side surfaces. The pair of inclined surfaces 21a, 21a is opposingly inclined to an advancing and retracting direction of the primary finger 21 (a direction along the central axis CL 21) and is tapered so that distance between the inclined surfaces 21a, 21a is decreased toward the tip of the primary finger 21. The inclined surfaces 21a, 21a of the primary finger 21 are opposingly inclined, but have the same angle of inclination (the angle of inclination to the central axis CL 1). The angle of inclination for the inclined surfaces 21a, 21a will be described later.

The central axis CL1 of the primary finger 21 is positioned along a front-rear direction of the pump body 11 (a direction orthogonal to a longitudinal direction of the infusion tube T mounted on the pump body 11, i.e., a direction orthogonal to the front wall 110 of the pump body 11). The primary finger 21 is slidably supported on a guide member 5 (see FIG. 5) and adapted to be capable of being advanced and retracted in the front-rear direction of the pump body 11. The guide member 5 is supported and fixed on the pump body 11.

Figure 4:
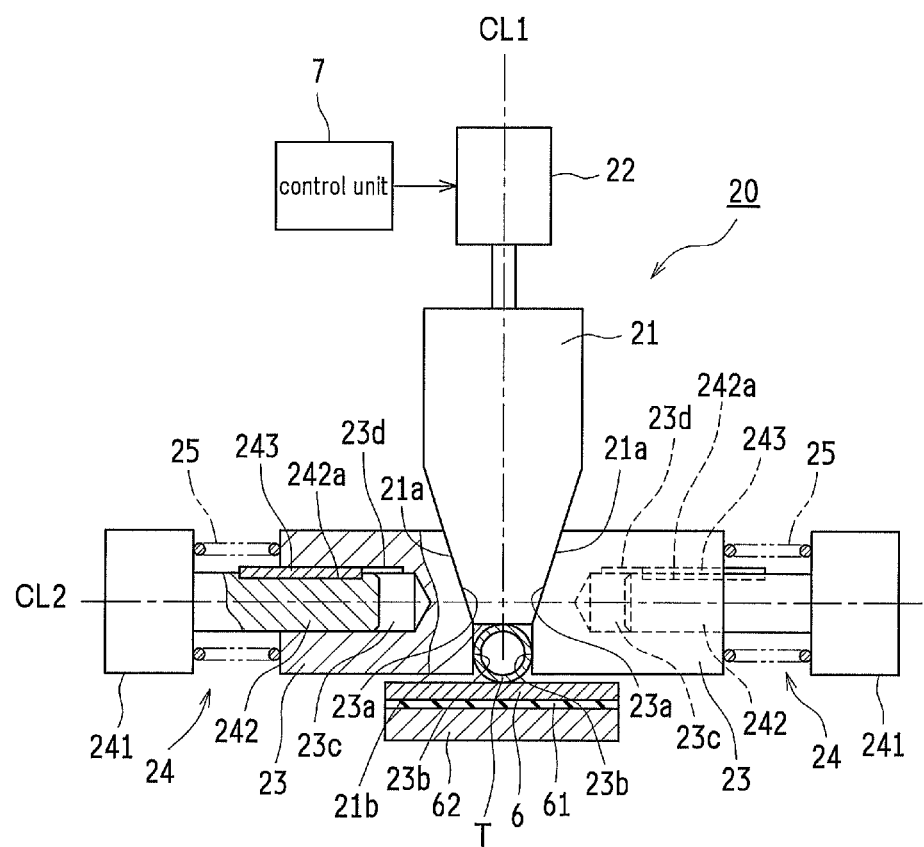
FIG. 4 A partially cut-away diagram taken along X-X of FIG. 3.
Figure 5:
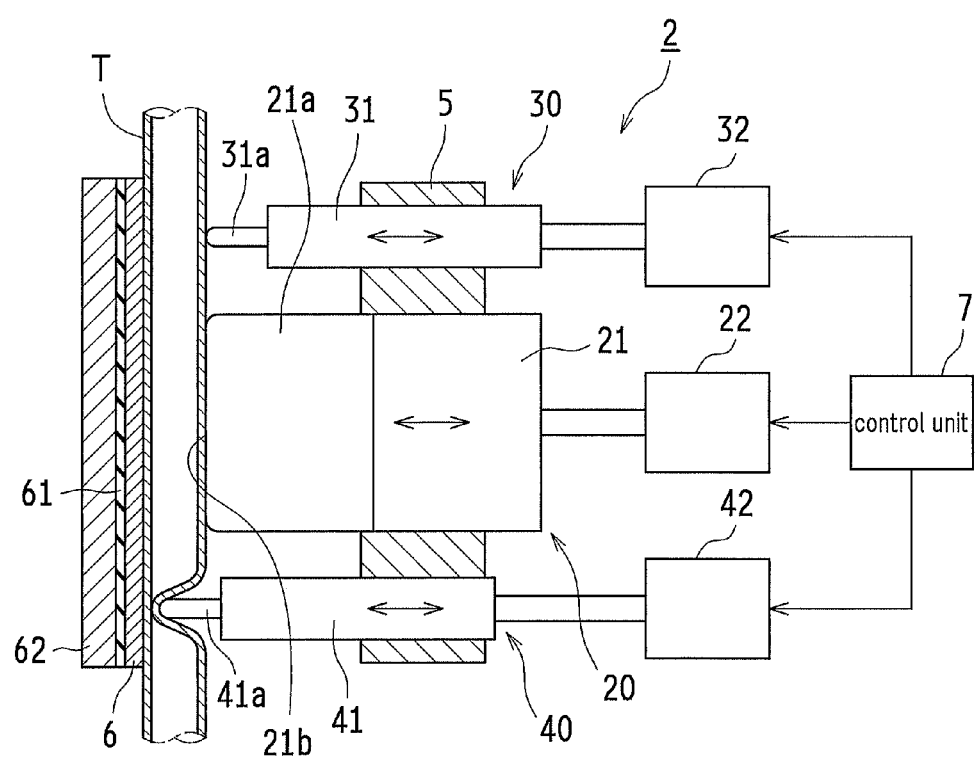
FIG. 5 A side view of an upstream side valve section, a tube pressing section and a downstream side valve section, which collectively constitute the pump mechanism.
Figure 6:
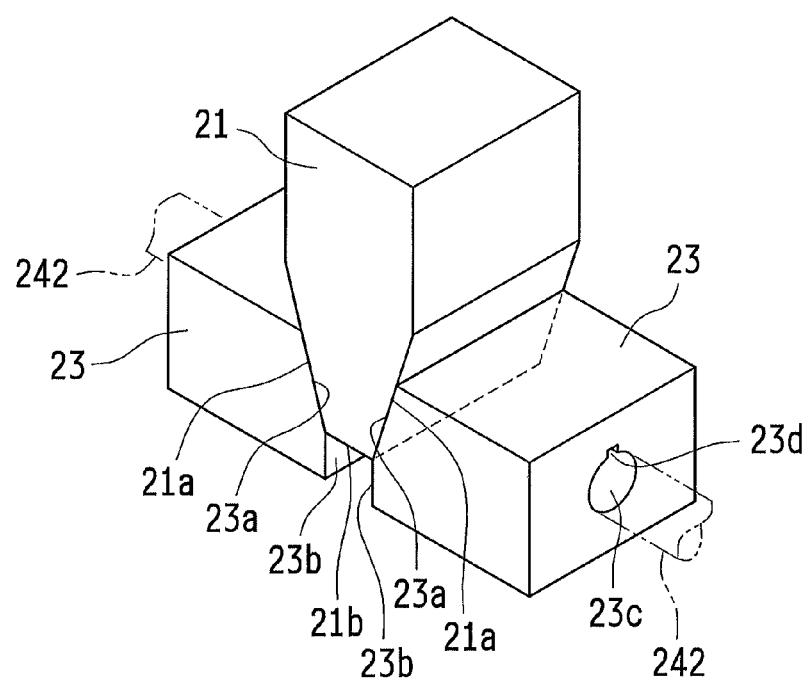
FIG. 6 A perspective view of only a primary finger and a pair of secondary fingers, which collectively constitute the tube pressing section.

An actuator 22 is connected to a rear end of the primary finger 21. Driving the actuator 22 causes the primary finger 21 to be advanced and retracted (the primary finger 21 moves forward and backward), and when the primary finger 21 is in its most retracted position the tip surface 21b of the primary finger 21 is positioned in contact with an outer peripheral surface of the infusion tube T (in a perfect circle) mounted on the pump body 11 (i.e., in a position corresponding to the outer peripheral surface of the infusion tube T) as shown in FIGS. 4 and 5. Furthermore, when the primary finger 21 is advanced from this state (in its most retracted position), the infusion tube T is pressed in the advancing process. Here, since the infusion pump 1 in this example is of the half-occlusion type, when the primary finger 21 is in its most advanced position, the stroke in advancing and retracting the primary finger 21 by the actuator 22 is set so that the infusion tube T is not fully occluded as shown in FIGS. 8(A) and 9(C).

Examples of the actuator 22 may include a mechanism in which a cam to drive the primary finger 21 to advance and retract and an electric motor to rotationally drive a cam shaft thereof are combined (see FIG. 19, for example), and a mechanism in which an electric motor and a rotation-translation mechanism (for example, a rack-and-pinion gear) are combined. An actuator which employs a solenoid as its drive source also may be possible.

The pair of secondary fingers 23, 23 is positioned on both sides of the primary finger 21 (between which the primary finger 21 is sandwiched). The pair of secondary fingers 23, 23 with the same shape and dimension is positioned bilaterally symmetrically. Each of the secondary fingers 23, 23 is a member with the rectangular cross section and they have inclined surfaces 23a, 23a sliding relative to the inclined surfaces 21a, 21a of the primary finger 21, respectively, which are provided on their tip portion. The angle of inclination for the inclined surfaces 23a, 23a of the secondary fingers 23, 23 will also be described later.

The central axis CL2 of the secondary fingers 23, 23 is positioned along a direction orthogonal to the central axis CL1 of the primary finger 21 (a direction parallel to the front wall 110 of the pump body 11). The secondary finger 23, 23 are also provided with guide through holes 23c, 23c extending along the central axis CL2. The inner diameter of each of the guide through holes 23c, 23c is set to be greater than an outer diameter of each of guide rods 242, 242 described later by a predetermined amount, so that the secondary fingers 23, 23 is adapted to be slidable relative to the guide rods 242, 242. The guide through holes 23, 23 is provided with slidable keyways 23d, 23d along which sliding key 243, 243 described later can slide.

The secondary fingers 23, 23 are slidably supported by the sliding support member 24, 24. The sliding support members 24, 24 have base members 241, 241 and the guide rods 242, 242 which are integrally provided thereon. The central axis of the guide rods 242, 242 is along the central axis CL2. The base members 241, 241 are supported and fixed on the pump body 11.

The guide rods 242, 242 have keyways 242a, 242a machined thereon and the sliding key 243, 243 are fitted into the keyways 242a, 242a. The guide rods 242, 242 are inserted into the guide through holes 23c, 23c of the secondary fingers 23, 23, and further the sliding keys 243, 243 of the guide rods 242, 242 are inserted into the keyways 23d, 23d of the guide through holes 23c, 23c. This restricts the movement (rotation) of the secondary fingers 23, 23 about the axis of the guide rods 242, 242 and the secondary fingers 23, 23 are adapted to be slidable (be advanced and retracted) only in an axial direction of the guide rods 242, 242, in other words, in one direction orthogonal to an advancing and retracting direction of the primary finger 21 (a tube pressing direction).

In addition, compression coil springs (resilient members) 25, 25 are sandwiched between the rear end surfaces of the mentioned secondary fingers 23, 23 and the base members 241, 241, and the resilient force of the compression coil springs 25, 25 presses the secondary fingers 23, 23 toward the primary finger 21, so that the inclined surfaces 23a, 23a of the secondary fingers 23, 23 are pressed and abut on the inclined surfaces 21a, 21a of the primary finger 21, respectively.

Thus, pressing the secondary finger 23, 23 by the compression coil springs 25, 25 in this way causes that in a process in which the primary finger 21 is advanced and retracted between its most retracted position and its most advanced position, the inclined surfaces 21a, 21a of the primary finger 21 and the inclined surfaces 23a, 23a of the secondary fingers 23, 23 slide in contact with each other, and the secondary fingers 23, 23 are moved in conjunction with the primary finger 21 being advancing and retracting because the inclined surfaces 23a, 23a of the secondary fingers 23, 23 are not separated from the inclined surfaces 21a, 21a of the primary finger 21.

In particular, when the primary finger 21 is advanced, the inclined surfaces 21a, 21a of the primary finger 21 and the inclined surfaces 23a, 23a of the secondary fingers 23, 23 slide relative to each other, and each of the secondary fingers 23, 23 is retracted in conjunction with the movement of the primary finger 21 (the pair of secondary fingers 23, 23 moves apart from each other). On the other hand, when the primary finger 21 is retracted, the resilient force of the compression coil spring 25 presses the secondary fingers 23, 23 toward the primary finger 21 and the inclined surfaces 21a, 21a of the primary finger 21 and the inclined surfaces 23a, 23a of the secondary fingers 23, 23 slide relative to each other, so that each of the secondary fingers 23, 23 is advanced in conjunction with the movement of the primary finger 21 (the pair of secondary fingers 23, 23 is moved in the direction to come close to each other).

—Angle of Inclination for Finger Inclined Surface—

Figure 25:
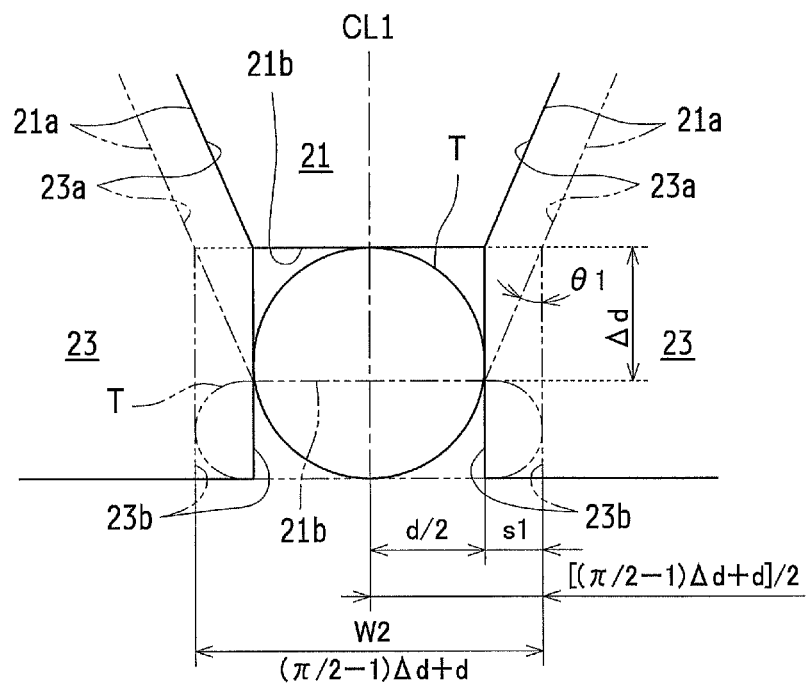
FIG. 25 A diagram illustrating an angle of inclination for inclined surfaces of the primary finger and the secondary fingers of the tube pressing section illustrated in FIG. 4.

Now, the angle of inclination for both of the inclined surface 21a of the primary finger 21 and the inclined surface 23a of the secondary finger 23 will be described with reference to FIG. 25.

Firstly, assuming that the outer diameter (diameter) of the infusion tube T in the perfect circle is designated as "d" and the amount of compression of the infusion tube T is designated as "Δd", an entire width W2 of the infusion tube T is expressed as: $[W2=(\pi/2-1)\Delta d+d]$. The angle of inclination θ1 for the inclined surfaces 21a, 21a of the primary finger 21 (the angle of inclination to the central axis CL1) θ1 may also be expressed: $[\tan\theta 1 = s1/\Delta d]$.

Where, $$s1 = W2/2 - d/2$$
$$= [(\pi/2-1)\Delta d + d]/2 - d/2$$
$$= (\pi/2-1)\Delta d/2,$$

and tan θ1 is expressed as below:

$$\tan\theta 1 = [(\pi/2-1)\Delta d/2]/\Delta d = \pi/4 - \frac{1}{2}.$$

θ1 is expressed as below:

$$\theta 1 = \tan^{-1}(\pi/4 - 1/2)$$
$$= 15.9°.$$

These calculated results show that setting the angle of inclination for the inclined surfaces 21a, 21a of the primary finger 21 to be "15.9°" as well as setting the angle of inclination for the inclined surfaces 23a, 23a of the secondary fingers 23, 23, which slide relative to the inclined surfaces 21a, 21a of the primary finger 21 (the angle of inclination to the central axis CL1 of the primary finger 21) to be "15.9°" causes that the secondary fingers 23, 23 to move in proportion to the variation $[(\pi/2-1)\Delta d+d]$ in the entire width of the infusion tube T deformed due to advancing and retracting the primary finger 21 (i.e., the secondary fingers 23, 23 move along CL2), thereby the occurrence of any gap between tip surfaces 23b, 23b of the secondary fingers 23, 23 and the outer peripheral surface of the infusion tube T in the advancing and retracting process of the primary finger 21 can be suppressed. Note that a movement amount of advancing and retracting the right secondary finger is same as that of the left one, and the double movement amount (2×Δα) is in proportion to the variation in the entire width of the infusion tube T: $[(\pi/2-1)\Delta d+d]$.

In this example, the angle of inclination for both of the inclined surface 21a of the primary finger 21 and the inclined surface 23a of the secondary finger 23 may be exactly "15.9°" or may be 16°±β (β=tolerance), for example.

—Valve Section—

Figure 3:
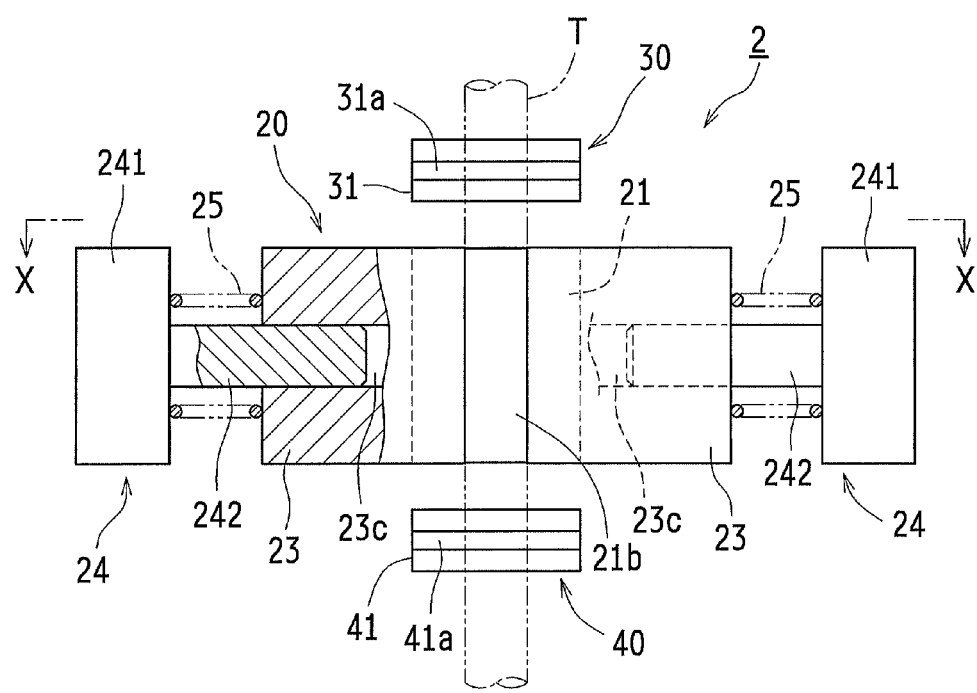
FIG. 3 A partially cut-away front view of a pump mechanism applied in the infusion pump in FIG. 1.

The upstream side valve section 30 and the downstream side valve section 40 will now be describe with reference to FIGS. 3 and 5, etc.

Firstly, the upstream side valve section 30 comprises the upstream side valve finger 31 and an actuator 32, etc.

The upstream side valve finger 31 is provided on the upstream side in the infusion delivery direction of the primary finger 21. The upstream side valve finger 31 is a member with a rectangular cross section and positioned along a direction parallel to the central axis CL1 of the primary finger 21. A projection 31a is also provided at a tip portion of the upstream side valve finger 31.

The upstream side valve finger 31 is slidably supported on the guide member 5 (same as the primary finger 21) and adapted to be capable of being advanced and retracted in the front-rear direction of the pump body 11 (in the direction orthogonal to the front wall 110 of the pump body 11) as in the primary finger 21.

Figure 7:
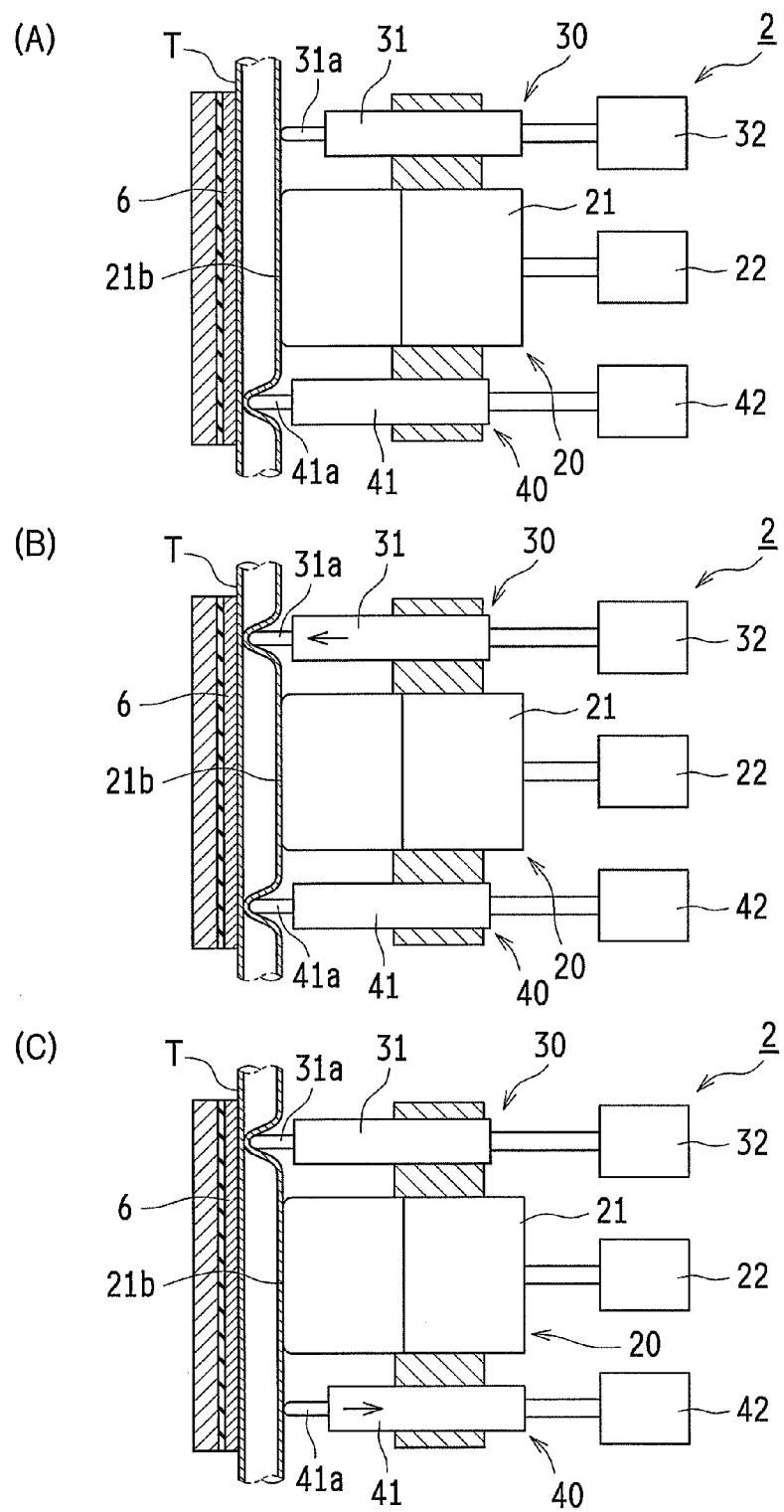
FIG. 7 Operation explanatory diagrams of the pump mechanism illustrated in FIG. 5.

The actuator 32 is connected to the rear end of the upstream side valve finger 31. Driving the actuator 32 causes the upstream side valve finger 31 to be advanced and retracted (the upstream side valve finger 31 is moved forward and backward), and when the upstream side valve finger 31 is in its most retracted position the tip of the upstream side valve finger 31 (the tip of the projection 31a) is placed in the position in contact with the outer peripheral surface of the infusion tube T (in the perfect circle) mounted on the pump body 11 (in the position corresponding to the outer peripheral surface of the infusion tube T), as shown in FIGS. 5 and 7(A). Furthermore, when the upstream side valve finger 31 is advanced from this state (its most retracted position), the infusion tube T is pressed in the advancing process and the infusion tube T is completely occluded with the upstream side valve finger 31 reaching its most advanced position, as shown in FIG. 7 (B).

Examples of the actuator 32 of this upstream side valve finger 31 also may include a mechanism in which a cam to drive the upstream side valve finger 31 to advance and retract and an electric motor to rotationally drive a cam shaft thereof are combined (see FIG. 19, for example), a mechanism in which an electric motor and a rotation-translation mechanism (for example, a rack-and-pinion gear) are combined. An actuator which employs a solenoid as its drive source also may be possible.

In addition, the downstream side valve section 40 comprises the downstream side valve finger 41 and an actuator 42, etc.

The downstream side valve finger 41 is provided on the downstream side in the infusion delivery direction of the primary finger 21. The downstream side valve finger 41 is a member with a rectangular cross section and positioned along the direction parallel to the central axis CL1 of the primary finger 21. A projection 41a is also provided at a tip portion of downstream side valve finger 41.

The downstream side valve finger 41 is slidably supported on the guide member 5 (same as the primary finger 21) and adapted to be capable of being advanced and retracted in the front-rear direction of the pump body 11 (in the direction orthogonal to the front wall 110 of the pump body 11) as in the primary finger 21.

The actuator 42 is connected to the rear end of the downstream side valve finger 41. Driving the actuator 42 causes the downstream side valve finger 41 to be advanced and retracted (the downstream side valve finger 41 is moved forward and backward), and when the downstream side valve finger 41 is its most retracted position the tip of the downstream side valve finger 41 (the tip of projection 41a) is placed in the position in contact with the outer peripheral surface of the infusion tube T (in the perfect circle) mounted on the pump body 11 (in the position corresponding to the outer peripheral surface of the infusion tube T), as shown in FIG. 7(C). Furthermore, when the downstream side valve finger 41 is advanced from this state (in its most retracted position), the infusion tube T is pressed in the advancing process and the infusion tube T is completely occluded with the downstream side valve finger 41 reaching its most advanced position, as shown in FIG. 8(B).

Examples of the actuator 42 of this downstream side valve finger 41 also may include, for example, a mechanism in which a cam to drive the downstream side valve finger 41 to advance and retract and an electric motor to rotationally drive a cam shaft thereof are combined (see FIG. 19, for example), a mechanism in which an electric motor and a rotation-translation mechanism (for example, a rack-and-pinion gear) are combined. An actuator which employs a solenoid as its drive source also may be possible.

The driving of each of the actuator 22 of the primary finger 21, the actuator 32 of the upstream side valve finger 31, and the actuator 42 of the downstream side valve finger 41 is controlled by a control unit 7. Note that each of the actuators 22, 32 and 42 (such as an electrical motor) is powered from any battery contained in the infusion pump 1 or any commercial power source.

Here, if the actuator 22 of the primary finger 21, the actuator 32 of the upstream side valve finger 31, and the actuator 42 of the downstream side valve finger 41 employ a mechanism in which a cam to drive each of fingers 21, 31 and 32 to be advanced and retracted and an electric motor to rotationally drive a cam shaft thereof are combined, the cam shaft for each of the actuators 22, 32 and 42 may be the common shaft which is rotationally driven by a single electric motor.

—Control Unit—

The control unit 7 is constituted mainly by a microcomputer etc. The control unit 7 is connected to, but not illustrated, an air bubble sensor (for example, an ultrasonic sensor) which detects air bubbles mixed into the infusion tube T mounted on the pump body 11, an open/close sensor which detects a closed state of the door 12, a distance sensor, etc. and output signals from each sensor are input to the control unit 7.

Note that the distance sensor detects a gap (distance) between the tip surface 21b of the primary finger 21 in its most retracted position and the tube pressing plate 6 on the door 12 side when the door 12 is closed. Examples of the distance sensor may include a reflective photoelectric sensor, a capacitance sensor or an ultrasonic sensor.

The control unit 7 controls each of the actuators 22, 32, 42 of the pump mechanism 2 by the action described later, in accordance with a set value for the rate of infusion (an delivery amount of infusion per unit time) which is set (input) through an operation panel 122 on a display operation unit 120 (see FIG. 1), as well as regulates variably the rate of infusion by controlling an interval of a solution delivery cycle (described later). In this example, the rate of infusion may be set every [1 mL/h] between 1 mL/h-1200 mL/h, for example.

In addition, the control unit 7 is configured to display, on a display panel 121 of the display operation unit 120, the operation information such as "a rate of infusion (infusion amount)" and "an accumulated infusion time" and to display various alerts including such as "Air Bubbles Containing Fault" and "Door Open" as well as to enable an alarm buzzer device.

—Operation Explanation of Pump Mechanism—

Figure 8:
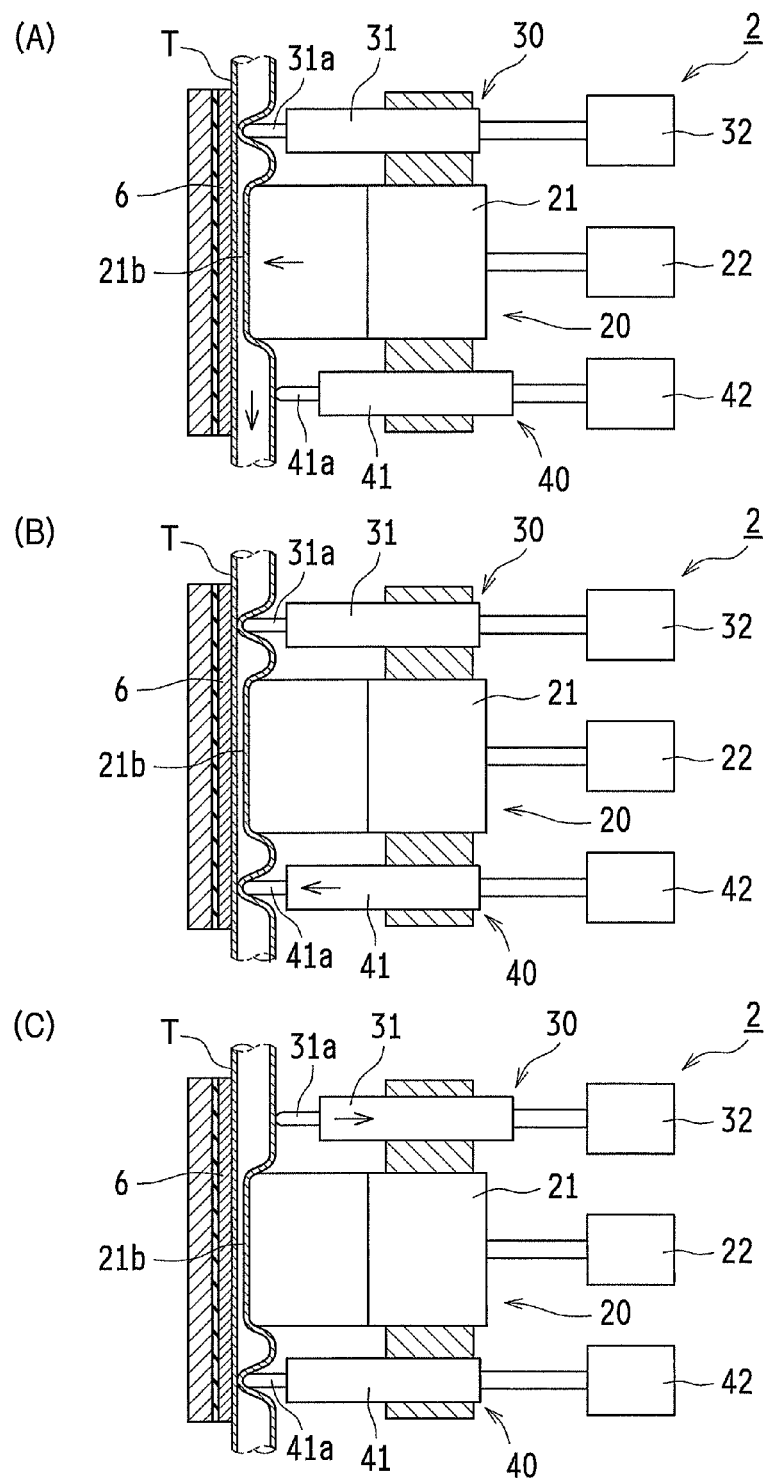
FIG. 8 Operation explanatory diagrams of the pump mechanism illustrated in FIG. 5.

Now, the operation of the pump mechanism 2 will be described with reference to FIGS. 7 and 8. Note that in FIGS. 7 and 8 the each finger is illustrated without cutting away.

[S1] Firstly, FIG. 7(A) shows the state in which the infusion tube T mounted on the pump body 11 with the door 12 closed (referred to as an "initial state"). In the initial state, only the downstream side valve finger 41 of the downstream side valve section 40 is in its most advanced position and the infusion tube T is fully occluded by the projection 41a of the downstream side valve finger 41.

[S2] From the state shown in FIG. 7(A), the actuator 32 of the upstream side valve finger 31 is driven to move the upstream side valve finger 31 to its most advanced position, thereby fully occluding the infusion tube T on the upstream side of the primary finger 21 of the tube pressing section 20 (the upstream side in the infusion delivery direction) (see, FIG. 7(B)).

[S3] As shown in FIG. 7(C), the actuator 42 of the downstream side valve finger 41 is driven to move the downstream side valve finger 41 in its most advanced position to its most retracted position, thereby opening the infusion tube T on the downstream side of the primary finger 21 (the downstream in the infusion delivery direction).

[S4] From the state shown in FIG. 7(C), the actuator 22 of the primary finger 21 is driven to advance the primary finger 21, thereby pressing the infusion tube T (FIG. 8(A)). The infusion solution within the infusion tube T is sent out to the downstream side by pressing the infusion tube T with the primary finger 21 in this way. Here, since the infusion pump 1 in this example is of the half-occlusion type, even if the primary finger 21 reaches its most advanced position, the infusion tube T is not fully compressed as shown in FIGS. 8(A) and 9(C).

[S5] From the state shown in FIG. 8(A), the actuator 42 of the downstream side valve finger 41 is driven to move the downstream side valve finger 41 to its most advanced position, thereby fully occluding the infusion tube T on the downstream side of the primary finger 21 (FIG. 8(B)).

[S6] From the state shown in FIG. 8(B), the actuator 32 of the upstream side valve finger 31 is driven to move the upstream side valve finger 31 to its most retracted position, thereby opening the infusion tube T on the upstream side of the primary finger 21 (FIG. 8(C)).

[S7] From the state shown in FIG. 8(C), the actuator 22 of the primary finger 21 is driven to move the primary finger 21 to its most retracted position, thereby restoring the initial state shown in FIG. 7(A).

One cycle for delivering the infusion solution is completed through the described operation, and the infusion solution within the infusion tube T can be continuously sent out to the downstream side by repeating this cycle sequentially. Thus, the rate of infusion can be variably regulated by controlling the interval of the solution delivery cycle.

—Operation Explanation of Primary Finger and Secondary Finger—

Figure 9:
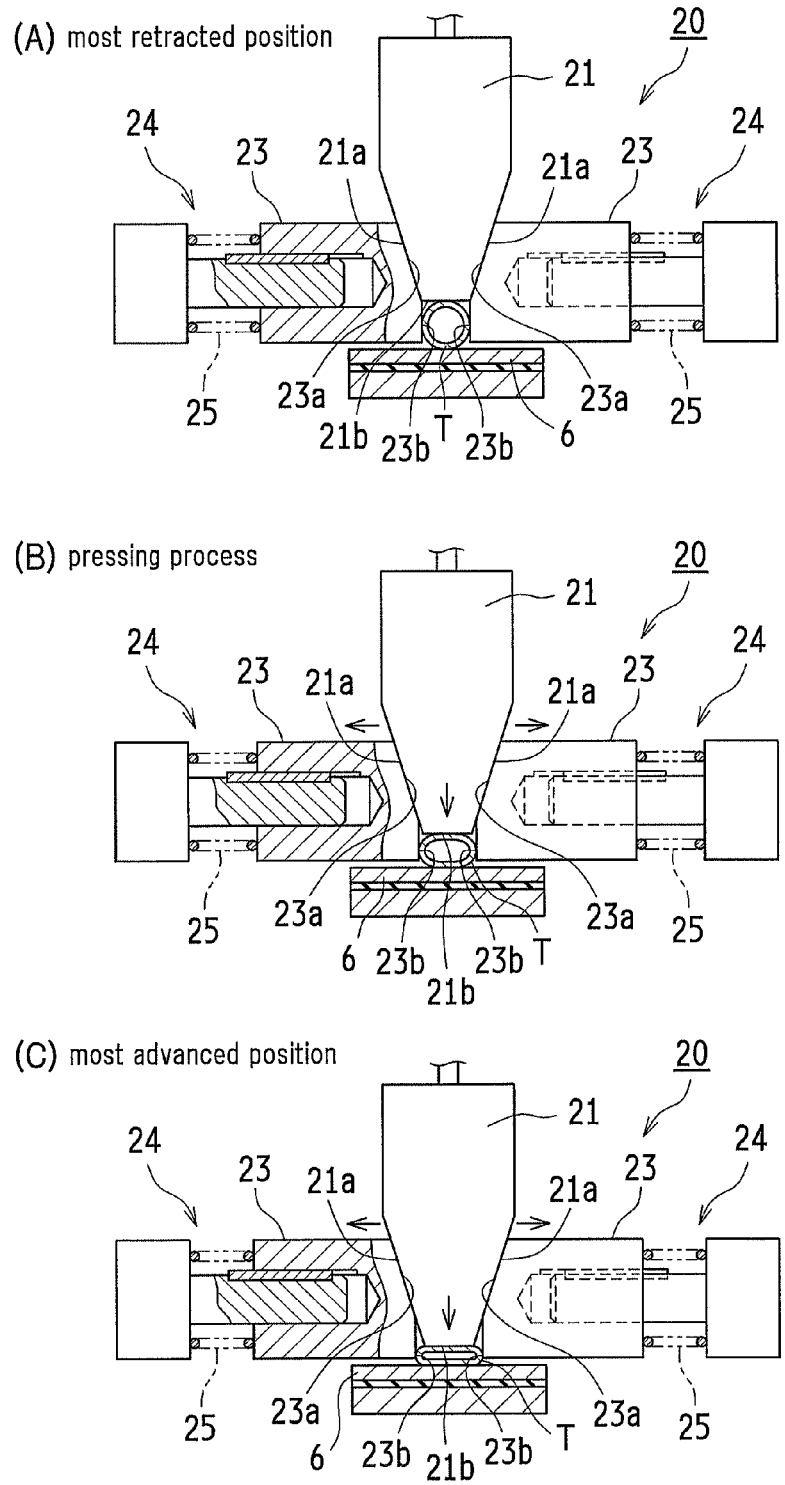
FIG. 9 Operation explanatory diagrams of the primary finger and the secondary fingers of the tube pressing section illustrated in FIG. 4.
Figure 10:
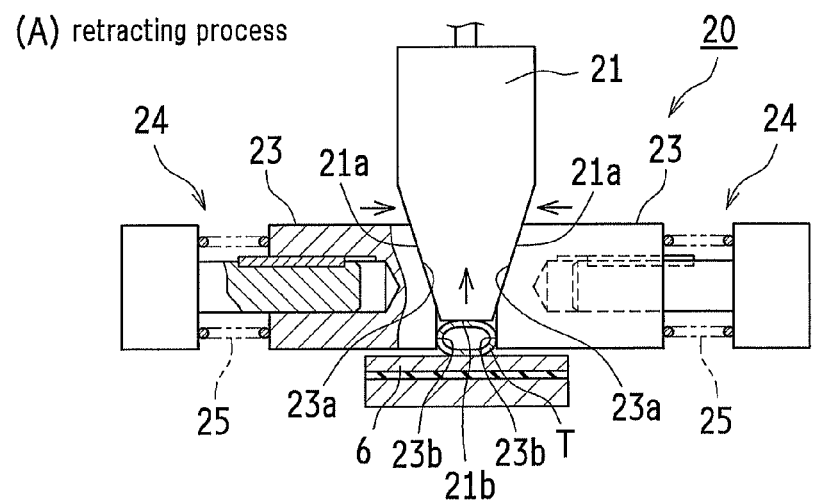
FIG. 10 Operation explanatory diagrams of the primary finger and the secondary fingers of the tube pressing section illustrated in FIG. 4.
Figure 10:
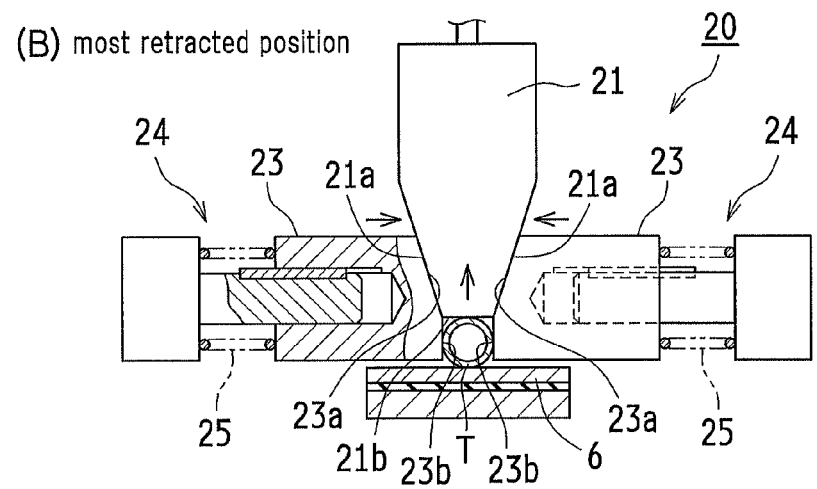

Next, the operation of the primary finger 21 and the pair of secondary fingers 23, 23 which collectively constitute the tube pressing section 20 will be described with reference to FIGS. 9 and 10. Note that in FIGS. 9 and 10, a pressing finger 21 etc. are illustrated without cutting away.

[S11] Firstly, as shown in FIG. 9(A), when the primary finger 21 is in its most retracted position (initial position), the tip surface 21b of the primary finger 21 and the tip surfaces 23b, 23b of the pair of secondary fingers 23, 23 are placed in the position in contact with the outer peripheral surface of the infusion tube T (in a position corresponding to the outer peripheral surface of the infusion tube T). Also the tube pressing plate 6 is in contact with the outer peripheral surface of the infusion tube T.

[S12] From the state shown in FIG. 9(A), when the actuator 22 of the primary finger 21 (see FIG. 4) is driven to advance the primary finger 21, the tip surface 21b of the primary finger 21 presses the infusion tube T, so that the infusion tube T is compressed (FIG. 9(B)). Moreover, in the advancing process of the primary finger 21, the sliding of the inclined surfaces 21a, 21a of the primary finger 21 and each of the inclined surfaces 23a, 23a of the secondary fingers 23, 23 relative to each other causes each of the secondary fingers 23, 23 to be moved (retracted) against the resilient force of the compression coil springs 25, 25 in a direction orthogonal to the tube pressing direction (along the central axis CL2 shown in FIG. 4). At this time, since the pair of secondary fingers 23, 23 is moved (retracted) in proportion to the variation (increasing) in the entire width of the infusion tube T deformed due to advancing the primary finger 21 (the entire width shown in FIG. 25: $(\pi/2-1)\Delta d+d$)) as described above, in the advancing process of the primary finger 21, the tip surfaces 23b, 23b of the secondary fingers 23, 23 are always placed in the position corresponding the outer peripheral surface (side surface) of the compressed infusion tube T.

[S13] From the state shown in FIG. 9(B), when the primary finger 21 is further advanced to reach its most advanced position, the infusion tube T is further pressed into the state shown in FIG. 9(C). That is to say, since the infusion tube T is not fully compressed (in the half-occluded state) even when the primary finger 21 is in its most advanced position, the settling of the infusion tube T can be suppressed. Also, since the pair of secondary fingers 23, 23 is moved (retracted) in proportion to the variation (increasing) in the entire width of the infusion tube T in this movement process of the primary finger 21 to its most advanced position, each of the tip surfaces 23b, 23b of the secondary fingers 23, 23 is placed in the position corresponding to the outer peripheral surface (side surface) of the compressed infusion tube T, with the primary finger 21 reaching its most advance position.

Note that the steps of [S12] and [S13] (the advancing of the primary finger 21) corresponds to the above mentioned step [S4].

[S14] From the state shown in FIG. 9(C) (in the most advanced position), the actuator 22 of the primary finger 21 is driven in an opposite direction to that in pressing the primary finger 21, thereby retracting the primary finger 21. As retracting of the primary finger 21 in this way, the compressed infusion tube T would be restored into the original shape due to the tube's own restoring force (resilient force) (FIG. 10(A)).

Here, since the inclined surfaces 23a, 23a of the secondary fingers 23, 23 are pressed against the inclined surfaces 21a, 21a of the primary finger 21 due to the resilient force of the compression coil springs 25, 25, and remains to slide relative to the inclined surfaces 21a, 21a of the primary finger 21, when the primary finger 21 is retracted, the pair of secondary fingers 23, 23 is moved (advanced) due to the resilient force of the compression coil springs 25, 25. At this time, since the pair of secondary fingers 23, 23 is advanced in proportion to the variation (decreasing) in the entire width of the infusion tube T deformed (restored) due to retracting the primary finger 21 (the entire width shown in FIG. 25: $(\pi/2-1)\Delta d+d$)), in the retracting process of the primary finger 21, the tip surfaces 23b, 23b of the secondary fingers 23, 23 are always placed in the position corresponding to the outer peripheral surface (side surface) of the infusion tube T in the restoring process. Accordingly, even when the infusion tube T is not well restored since the side surface of the infusion tube T is pressed by the secondary fingers 23, 23, the infusion tube T would be restored.

[S15] From the state shown in FIG. 10(A), when the primary finger 21 is further retracted to reach its most retracted position, the state shown in FIG. 10(B) is achieved. That is to say, the infusion tube T is fully restored into the original shape (into the substantially perfect circular shape). Also in this movement process of the primary finger 21 to its most retracted position, since the pair of secondary fingers 23, 23 is moved in proportion to the variation (decreasing) in the entire width of the infusion tube T, the tip surfaces 23b, 23b of the secondary fingers 23, 23 are placed in the position corresponding to the outer peripheral surface (side surface) of the restored infusion tube T, with the primary finger 21 reaching its most retracted position. Accordingly, even when the infusion tube T is not well restored since the side surface of the infusion tube T is forcedly pressed by the secondary fingers 23, 23, the infusion tube T can be restored into the substantially perfect circular shape. Note that the steps of [S14] and [S15] (the retracting of the primary finger 21) corresponds to the above mentioned step [S7].

As discussed above, according to the infusion pump 1 in this example, in the advancing and retracting process of the primary finger 21, since the pair of secondary fingers 23, 23 is moved in proportion to the variation in the entire width of the infusion tube T, the occurrence of any gap between each of the tip surfaces 23b, 23b of the secondary fingers 23, 23 and the outer peripheral surface (side surface) of the infusion tube T can be suppressed. This can prevent the infusion tube T from meandering between the tip surface 21b of the primary finger 21 and the tube pressing plate 6, and the accuracy of the rate of infusion can be improved.

Moreover, since the sliding of the primary finger 21 and the secondary fingers 23, 23 (the sliding of their inclined surfaces) causes the secondary fingers 23, 23 to move, only one driving system is required for the fingers (only one driving system is required for the primary finger 21) and the reduction in cost can be contemplated. Also, it is advantageously in that the phase shift between the movement of the primary finger 21 and the movement of the secondary fingers 23, 23 is not likely to occur comparing to the conventional driving method described above, i.e., the method of driving individually the primary and secondary fingers or the method of driving each of the primary and secondary fingers by the respective cam shaft.

Note that, in the example discussed above, any guide member may be provided in order to avoid the positional shift between the primary finger 21 and each of the secondary fingers 23, 23, i.e., the positional shift in the longitudinal direction of the infusion tube T mounted on the pump body 11 (the positional shift in the vertical direction in FIG. 3).

Here, in the above example, although the single primary finger 21 is provided between the upstream side valve finger 31 and the downstream side valve finger 41, this invention is not limited thereto and a plurality of primary fingers 21 . . . 21 may be provided between the upstream side valve finger 31 and the downstream side valve finger 41.

In the above example, although the pump mechanism is configured so that the secondary fingers 23, 23 (the inclined surfaces 23a, 23a) are pressed against the inclined surfaces 21a, 21a of the primary finger 21 with the compression coil spring 25, and the resilient force of the compression coil spring 25 during retracting the primary finger 21 causes the inclined surfaces 21a, 21a of the primary finger 21 and the inclined surfaces 23a, 23a of the secondary fingers 23, 23 to slide relative to each other, alternatively the pump mechanism may be configured so that connecting means which slidably connects the primary finger 21 and the secondary fingers 23, 23 is provided, and the inclined surfaces 21a, 21a of the primary finger 21 and the inclined surfaces 23a, 23a of the secondary fingers 23, 23 slide relative to each other during the primary finger 21 is retracted.

Figure 11:
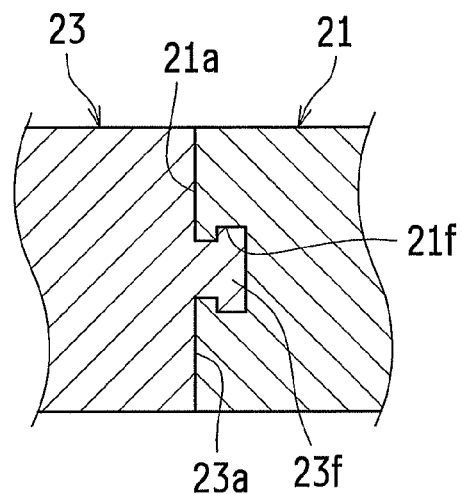
FIG. 11 A cross sectional view illustrating an example of connecting means which slidably connects the primary finger and the secondary finger.
Figure 11:
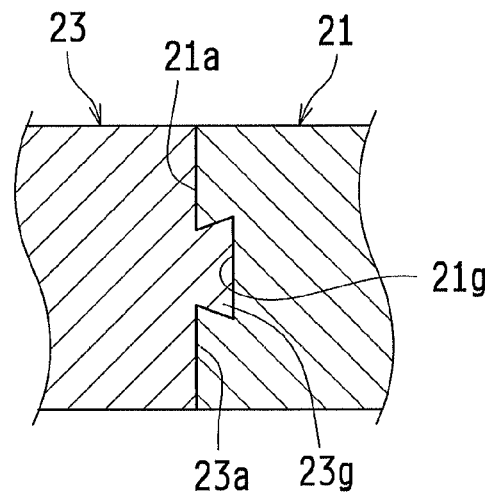

A particular configuration of the connecting means may involve, for example, the configuration as shown in FIG. 11(A) in which a T-shaped groove 21f is formed in the primary finger 21 while a T-shaped slider 23f is provided on the secondary finger 23, so that the primary finger 21 and the secondary finger 23 are slidably connected. In this case, the T-shaped groove provided in the secondary finger 23 and the T-shaper slider provided on the primary finger 21 may be involved. In addition, as shown in FIG. 11(B), another configuration can be employed in which a trapezoidal-shaped groove 21g is formed in the primary finger 21 and a trapezoidal-shaped slider 23g is provided on the secondary finger 23, so that the primary finger 21 and the secondary finger 23 are slidably connected. In this case, the trapezoidal-shaped groove provided in the secondary finger 23 and the trapezoidal-shaped slider provided on the primary finger 21 may be involved.

In addition, the structure which allows the secondary finger 23 to slide relative to the pump body 11 (slide in the direction along the central axis CL2) is not limited to that of FIG. 4, and other structures may be employed. For example, a structure in which a guide rod 242 is spline machined, or a structure in which the secondary finger 23 is slidably supported on the pump body 11 by use of the connecting mechanism shown in FIG. 11 (the connecting mechanism in which the T-shaped groove and the T-shaped slider are combined and the connecting mechanism in which the trapezoidal-shaped groove and the trapezoidal-shaped slider are combined) may be involved.

Note that, although in this example the half-occlusion type infusion pump 1 is described to which the present invention is applied, the present invention is not limited thereto, and the full-press type infusion pump whose infusion tube T is fully occluded by the primary finger 21 can be applied.

Embodiment 2

Figure 13:
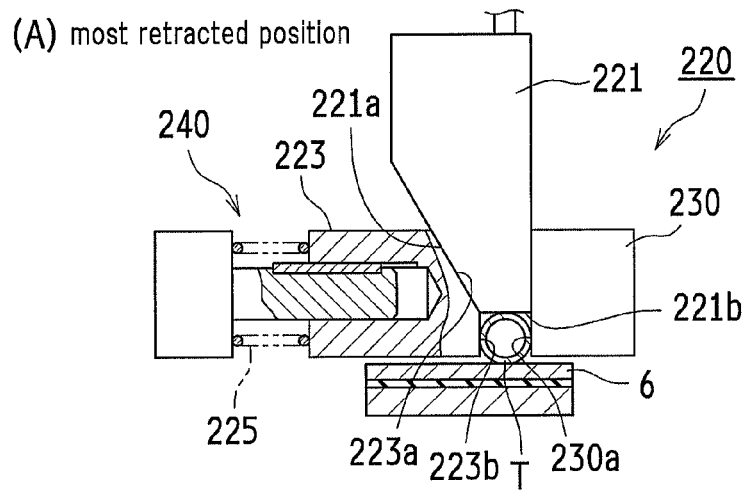
FIG. 13 Operation explanatory diagrams of the primary finger and the secondary finger of the tube pressing section illustrated in FIG. 12.
Figure 13:
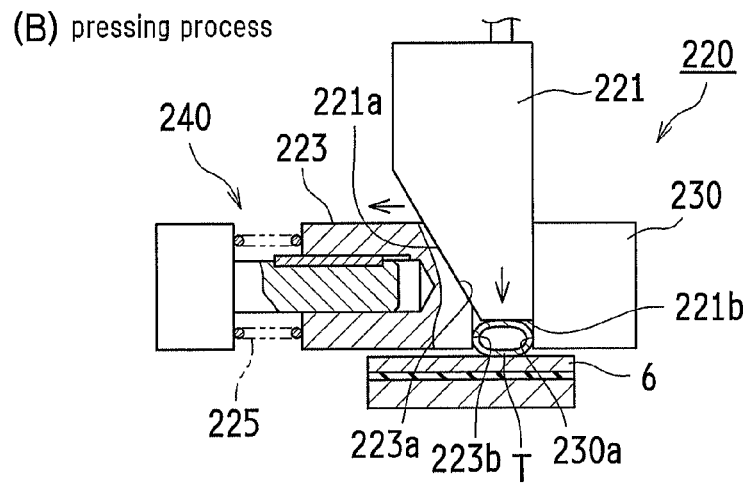
Figure 13:
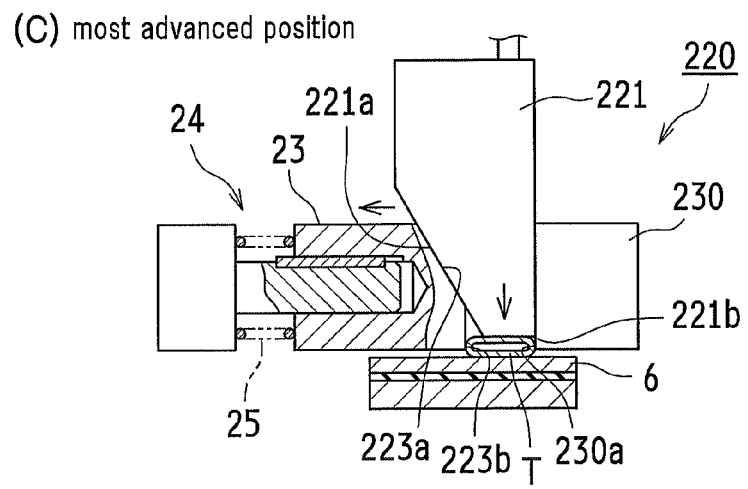
Figure 14:
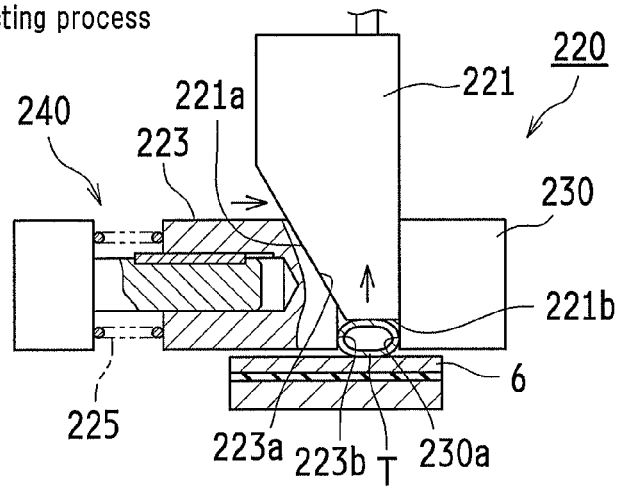
FIG. 14 Operation explanatory diagrams of the primary finger and the secondary finger of the tube pressing section illustrated in FIG. 12.
Figure 14:
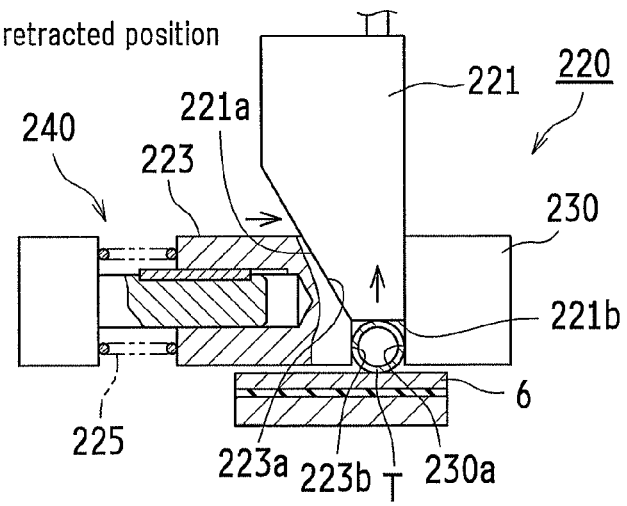
Figure 15:
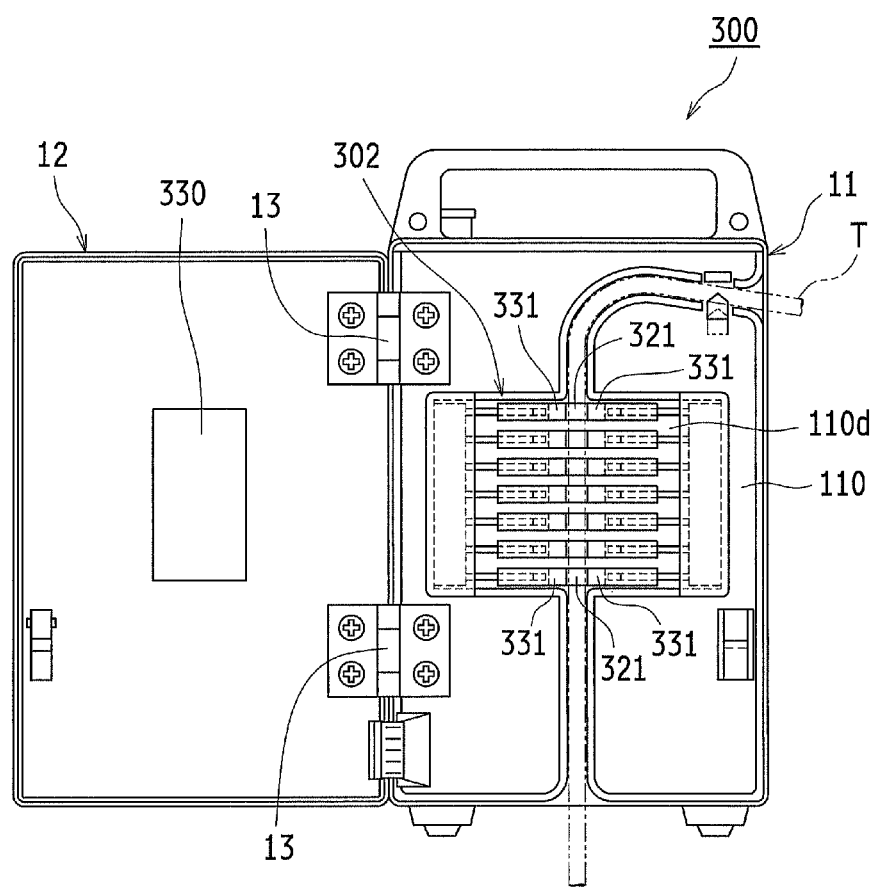
FIG. 15 A schematic configuration diagram of the other example of the infusion pump according to the present invention, with the door of the infusion pump opened.

Referring to the FIGS. 12-14, another example of the infusion pump according to the present invention will be described.

In the infusion pump in this example, the configuration other than a tube pressing section 220 (pump mechanism) described below is essentially same as that of the above [Embodiment 1], and accordingly will not be described in detail.

The tube pressing section 220 comprises a primary finger 221, an actuator 222, a secondary finger 223, a fixed finger 230, a sliding support member 240, a compression coil spring 225 etc. and the technical feature of the tube pressing section 220 is in that a single secondary finger 223 is provided for a single primary finger 221.

The primary finger 221 is a member with a rectangular cross section and has an inclined surface 221a provided on one side surface thereof. The inclined surface 221a is inclined to an advancing and retracting direction of the primary finger 221 (a direction along the central axis CL1). An angle of inclination for the inclined surface 221a will be described later. Another side surface of the primary finger 221 constitutes a plane (vertical plane 221c) parallel to its advancing and retracting direction (the direction along the central axis CL1).

Figure 2:
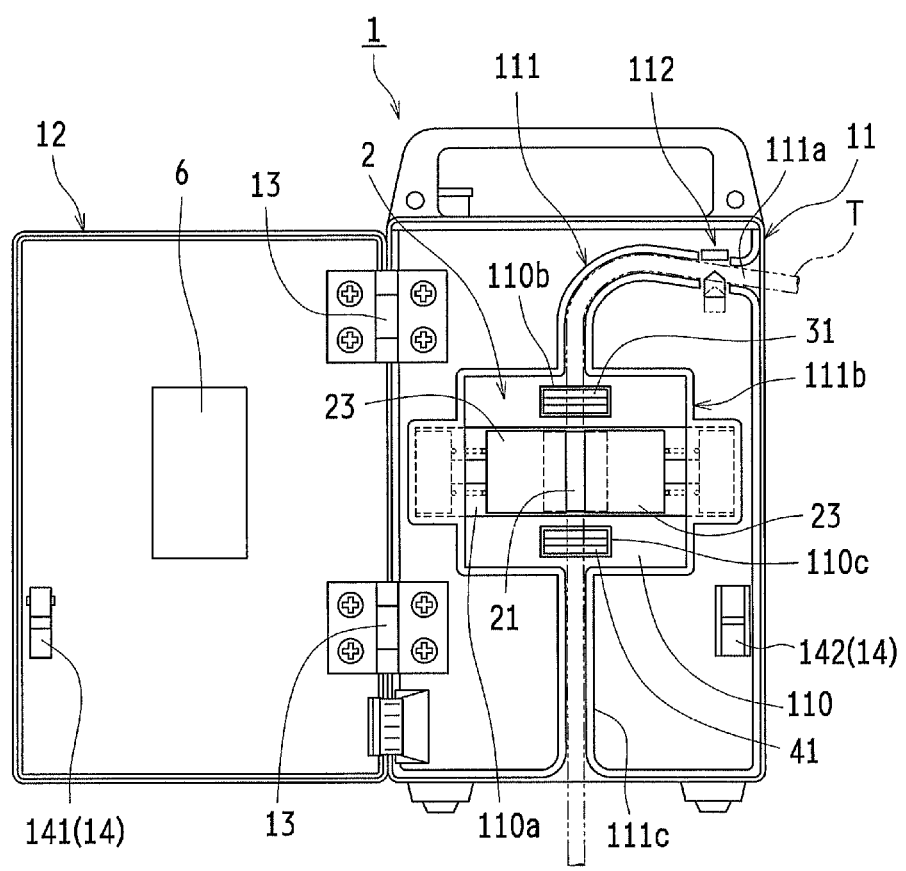
FIG. 2 A schematic configuration diagram illustrating an example of the infusion pump according to the present invention, with a door of the infusion pump opened.

This vertical plane 221c is adapted to be slidable relative to a tip surface 230a of the fixed finger 230 which is supported and fixed on the pump body 11 (see FIG. 2). The tip surface 230a of the fixed finger 230 acts as a restriction surface which restricts a position of the side surface of the infusion tube T.

The central axis CL21 of the primary finger 221 is positioned along the front-rear direction of the pump body 11 (see FIG. 2) (the direction orthogonal to the longitudinal direction of the infusion tube T mounted on the pump body 11, i.e., the direction orthogonal to the front wall 110 of the pump body 11). The primary finger 221 is slidably supported on a member (not shown) similar to the guide member 5 shown in FIG. 5 and adapted to be capable of being advanced and retracted along the front-rear direction of the pump body 11.

An actuator 222 is connected to a rear end of the primary finger 221. Driving the actuator 222 causes the primary finger 221 to advanced and retracted (the primary finger 221 moves forward and backward), and when the primary finger 221 is in its most retracted position the tip surface 221b of the primary finger 221 is placed in the position in contact with the outer peripheral surface of the infusion tube T (in the perfect circle) mounted on the pump body 11 (i.e., in the position corresponding to the outer peripheral surface of the infusion tube T) as shown in FIGS. 12 and 13(A). Furthermore, when the primary finger 221 is advanced from this state (in its most retracted position), the infusion tube T is pressed in the advancing process. Here, since the infusion pump 1 in this example is of the half-occlusion type, when the primary finger 221 is in its most advanced position, the stroke in advancing and retracting the primary finger 21 by the actuator 222 is set so that the infusion tube T is not fully occluded as shown in FIG. 13(C).

Examples of the actuator 222 may include those which combine an electric motor and a rotation-translation mechanism (for example, a rack-and-pinion gear), and an actuator which employs a solenoid as its driving source etc. Note that the actuator 222 is controlled by the control unit 7 in the same manner as in the [Embodiment 1]. The configuration and control operation of the control unit 7 is essentially same as in [Embodiment 1], and accordingly will not be described in detail.

The secondary finger 223 is positioned on one side of the primary finger 221. The secondary finger 223 is a member with the rectangular cross section and has an inclined surface 223a sliding relative to the inclined surface 221a of the primary finger 221, which is provided on its tip portion (the primary finger 221 side end). The angle of inclination for an inclined surface 223a of the secondary finger 223 will also be described later.

The central axis CL22 of the secondary fingers 223 is positioned along a direction orthogonal to the central axis CL21 of the primary finger 221 (a direction parallel to the front surface of the pump body 11). The secondary finger 223 is also provided with a guide through hole 223c extending along the central axis CL22. The inner diameter of the guide through hole 223c is set to be greater than an outer diameter of the guide rod 242 described later by a predetermined amount, so that the secondary finger 223 is adapted to be slidable relative to the guide rod 242. The guide through hole 223c is provided with a keyway 223d along which a sliding key 243 described later can slide.

The secondary finger 223 is slidably supported by the sliding support member 240. The sliding support member 240 has a base member 241 and the guide rod 242, which are integrally provided thereon. The central axis of the guide rod 242 is along the central axis CL22 of the secondary finger 223. The base member 241 is supported and fixed on the pump body 11.

The guide rod 242 has a keyway 242a machined thereon and the sliding key 243 is fitted into the keyway 242a. The guide rod 242 is inserted into the guide through hole 223c of the secondary finger 223, and further the sliding key 243 of the guide rod 242 is inserted into the keyway 223d of the guide through hole 223c. This restricts the movement (rotation) of the secondary finger 223 about the axis of the guide rod 242 and the secondary finger 223 can slide (advance and retract) only in the axial direction of the guide rod 242 i.e., in one direction orthogonal to an advancing and retracting direction of the primary finger 221).

In addition, a compression coil spring (resilient member) 225 is sandwiched between the rear end surface of the mentioned secondary finger 223 and the base member 241, and the resilient force of the compression coil spring 225 presses the secondary finger 223 toward the primary finger 221, so that the inclined surface 223a of the secondary finger 223 is pressed and abuts on the inclined surface 221a of the primary finger 221.

Thus, pressing the secondary finger 223 by the compression coil spring 225 in this way causes that in a process in which the primary finger 221 is advanced and retracted between its most retracted position and its most advanced position, the inclined surface 221a of the primary finger 221 and the inclined surface 223a of the secondary finger 223 slide in contact with each other, and the secondary finger 223 is moved in conjunction with the primary finger 221 being advanced and retracted because the inclined surface 223a of the secondary finger 223 is not separated from the inclined surface 221a of the primary finger 221.

In particular, when the primary finger 221 is advanced, the inclined surface 221a of the primary finger 221 and the inclined surface 223a of the secondary finger 223 slide relative to each other, and the secondary finger 223 is retracted in conjunction with the movement of the primary finger 221 (the secondary finger 223 moves apart from the fixed finger 230). On the other hand, when the primary finger 221 is retracted, the resilient force of the compression coil spring 225 presses the secondary finger 223 toward the primary finger 221 and the inclined surface 221a of the primary finger 221 and the inclined surface 223a of the secondary finger 223 slide relative to each other, so that the secondary finger 223 is advanced in conjunction with the movement of the primary finger 221 (the secondary finger 223 moves in the direction to be close to the fixed finger 230).

—Angle of inclination for Finger Inclined Surface—

Figure 26:
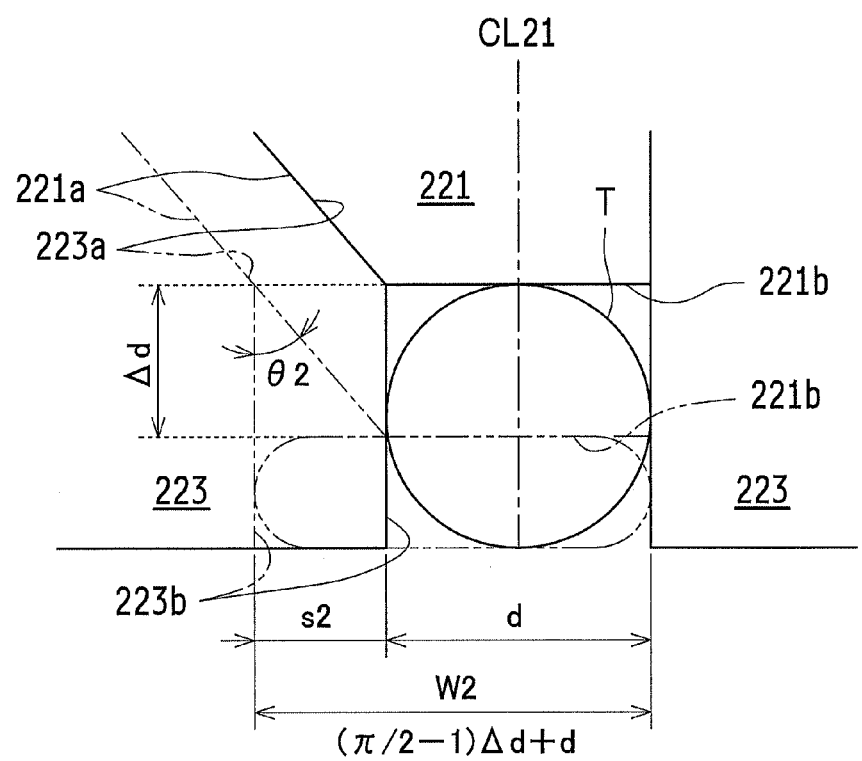
FIG. 26 A diagram illustrating an angle of inclination for inclined surfaces of the primary finger and the secondary finger of the tube pressing section illustrated in FIG. 12.

Now, the angle of inclination for the inclined surface 221a of the primary finger 221 and the inclined surface 223a of the secondary finger 223 will be described with reference to FIG. 26.

Firstly, assuming that an outer diameter (diameter) of the infusion tube T in the perfect circle is designated as "d" and an amount of compression of the infusion tube T is designated as "Δd", an entire width W2 of the infusion tube T is expressed as: [W2=(π/2−1)Δd+d]. The angle of inclination θ2 for the inclined surfaces 221a of the primary finger 221 (the angle of inclination to the central axis CL21) θ2 may also be expressed: [tan θ2=s2/Δd].

Where, $$s2 = [(\pi/2 - 1)\Delta d + d] - d$$
$$= (\pi/2 - 1)\Delta d,$$

tan θ2 is expressed as below:

tan θ2=(π/2−1)Δd/Δd=π/2−1, and

θ2 is expressed as below:

$$\theta 2 = \tan^{-1}(\pi/2 - 1)$$
$$= 29.7°.$$

These calculated results show that setting the angle of inclination for the inclined surface 221a of the primary finger 221 to be "29.7°" as well as setting the angle of inclination for the inclined surface 223a of the secondary finger 223, which slides relative to the inclined surface 221a of the primary finger 221 (the angle of inclination to the central axis CL21 of the primary finger 221) to be "29.7°" causes that the secondary finger 223 to move in proportion to the variation in the entire width of the infusion tube T [(π/2−1)Δd+d] deformed due to advancing and retracting the primary finger 221 (i.e., the secondary finger 223 moves along CL22), thereby the occurrence of any gap between the tip surface 223b of the secondary finger 223 and the outer peripheral surface of the infusion tube T in the advancing and retracting process of the primary finger 221 can be suppressed. In this example, the angle of inclination for both of the inclined surface 221a of the primary finger 221 and the inclined surface 223a of the secondary finger 223 may be exactly "29.7°" or may be the 30°±β (β=tolerance), for example.

—Operation Explanation of Primary Finger and Secondary Finger—

Next, the operation of the primary finger 221 and the secondary finger 223 which collectively constitute the tube pressing section 220 will be described with reference to FIGS. 13 and 14.

[S21] Firstly, as shown in FIG. 13(A), when the primary finger 221 is in its most retracted position (initial position), the tip surface 221b of the primary finger 221 and the tip surface 223b of the secondary fingers 223 are placed in the position in contact with the outer peripheral surface of the infusion tube T (in a position corresponding to the outer peripheral surface of the infusion tube T). Also the tip surface 230a of the fixed finger 230 is in contact with the outer peripheral surface of the infusion tube T and the tube pressing plate 6 is contact with the outer peripheral surface of the infusion tube T.

[S22] From the state shown in FIG. 13(A), when the actuator 222 of the primary finger 221 (see FIG. 12) is driven to advance the primary finger 221, the tip surface 221b of the primary finger 221 presses the infusion tube T, so that the infusion tube T is compressed (FIG. 13(B)). Note that, in the pressing process by the primary finger 221, the side surface of the infusion tube T (the side surface opposite to the secondary finger 223) is restricted by the tip surface 230a of the fixed finger 230.

Moreover, in the advancing process of the primary finger 221, the sliding of the inclined surface 221a of the primary finger 221 and the inclined surface 223a of the secondary finger 223 relative to each other causes the secondary finger 223 to be moved (retracted) against the resilient force of the compression coil spring 225 in the direction orthogonal to the tube pressing direction (along central axis CL2 shown in FIG. 4). At this time, since secondary finger 223 is moved (retracted) in proportion to the variation (increasing) in the entire width of the infusion tube T deformed due to advancing the primary finger 221 (the entire width shown in FIG. 26: $(\pi/2-1)\Delta d+d$)) as described above, in the advancing process of the primary finger 221, the tip surface 223b of the secondary finger 223 is always placed in the position corresponding the outer peripheral surface (side surface) of the infusion tube T.

[S23] From the state shown in FIG. 13(B), when the primary finger 221 is further advanced to reach its most advanced position, the infusion tube T is further pressed into the state shown in FIG. 13(C). That is to say, since the infusion tube T is not fully compressed (in the half-occluded state) even when the primary finger 221 is in its most advanced position, the settling of the infusion tube T can be suppressed. Also, since the secondary finger 223 is moved (retracted) in proportion to the variation (increasing) in the entire width of the infusion tube T in this movement process of the primary finger 221 to its most advanced position, the tip surface 223b of the secondary finger 223 is placed in the position corresponding to the outer peripheral surface (side surface) of the compressed infusion tube T, with the primary finger 221 reaching its most advance position.

[S24] From the state shown in FIG. 13(C) (in the most advanced position), the actuator 222 of the primary finger 221 is driven in an opposite direction to that in pressing the primary finger 221, thereby retracting the primary finger 221. As this retracting of the primary finger 221 in this way, the compressed infusion tube T would be restored into the original shape due to the tube's own restoring force (resilient force) (FIG. 14(A)).

Here, since the inclined surface 223a of the secondary finger 223 is pressed against the inclined surface 221a of the primary finger 221 due to the resilient force of the compression coil spring 225, and remains to slide relative to the inclined surface 221a of the primary finger 221, when the primary finger 221 is retracted, the secondary finger 223 is moved (advanced) due to the resilient force of the compression coil spring 225. At this time, since the secondary finger 223 is advanced in proportion to the variation (decreasing) in the entire width of the infusion tube T deformed (restored) due to retracting the primary finger 221 (the entire width shown in FIG. 26: $(\pi/2-1)\Delta d+d$)), in the retracting process of the primary finger 221, the tip surface 223b of the secondary finger 223 is always positioned corresponding to the outer peripheral surface (side surface) of the infusion tube T in the restoring process. Accordingly, even when the infusion tube T is not well restored since the side surface of the infusion tube T is pressed by the secondary finger 223, the infusion tube T would be restored.

[S25] From the state shown in FIG. 14(A), when the primary finger 221 is further retracted to reach its most retracted position, the state shown in FIG. 14(B) is achieved. That is to say, the infusion tube T is fully restored into the original shape (into the substantially perfect circular shape). Also in this movement process of the primary finger 221 to its most retracted position, since the secondary finger 223 is advanced in proportion to the variation (decreasing) in the entire width of the infusion tube T, the tip surface 223b of the secondary finger 223 is placed in the position corresponding to the outer peripheral surface (side surface) of the infusion tube T, with the primary finger 221 reaching its most retracted position. Accordingly, even when the infusion tube T is not well restored since the side surface of the infusion tube T forcedly pressed by the secondary finger 223, the infusion tube T can be restored into the substantially perfect circular shape.

As discussed above, according to the infusion pump in this example, in the advancing and retracting process of the primary finger 221, since the secondary finger 223 is moved in proportion to the variation in the entire width of the infusion tube T, the occurrence of any gap between the tip surface 223b of the secondary finger 223 and the outer peripheral surface (side surface) of the infusion tube T can be suppressed. This can prevent the infusion tube T from meandering between the tip surface 221b of the primary finger 221 and the tube pressing plate 6 and the accuracy of the rate of infusion can be improved.

Moreover, since the sliding of the primary finger 221 and the secondary finger 223 (the sliding of their inclined surfaces) relative to each other causes the secondary finger 223 to move, a single driving system is required for the fingers (only one system is required for the primary finger 221) and the reduction in cost can be contemplated. Also, it is advantageously in that the phase shift between the movement of the primary finger 221 and the movement of the secondary finger 223 is not likely to occur comparing to the conventional driving method described above, i.e., the method wherein the primary finger and the secondary finger are driven individually or the method wherein each of the primary and secondary fingers is driven by the respective cam shaft.

Note that, in the example discussed above, any guide member may be provided in order to avoid the positional shift between the primary finger 221 and the secondary finger 223 (the positional shift in the longitudinal direction of the infusion tube T mounted on the pump body 11).

Here, in the above example, although the single primary finger 221 is provided between the upstream side valve finger 31 and the downstream side valve finger 41, this invention is not limited thereto and a plurality of primary fingers 221 . . . 221 may be provided between the upstream side valve finger 31 and the downstream side valve finger 41.

Also in the above example, instead of the compression coil spring 225, the connecting structure similar to those in FIGS. 11(A) and 11(B) (the connecting structure which slidably connects the primary finger 221 and the secondary finger 223 such as [the T-shaped groove+the T-shaped slider], [the trapezoidal-shaped groove and the trapezoidal-shaped slider]) may be employed.

Figure 12:
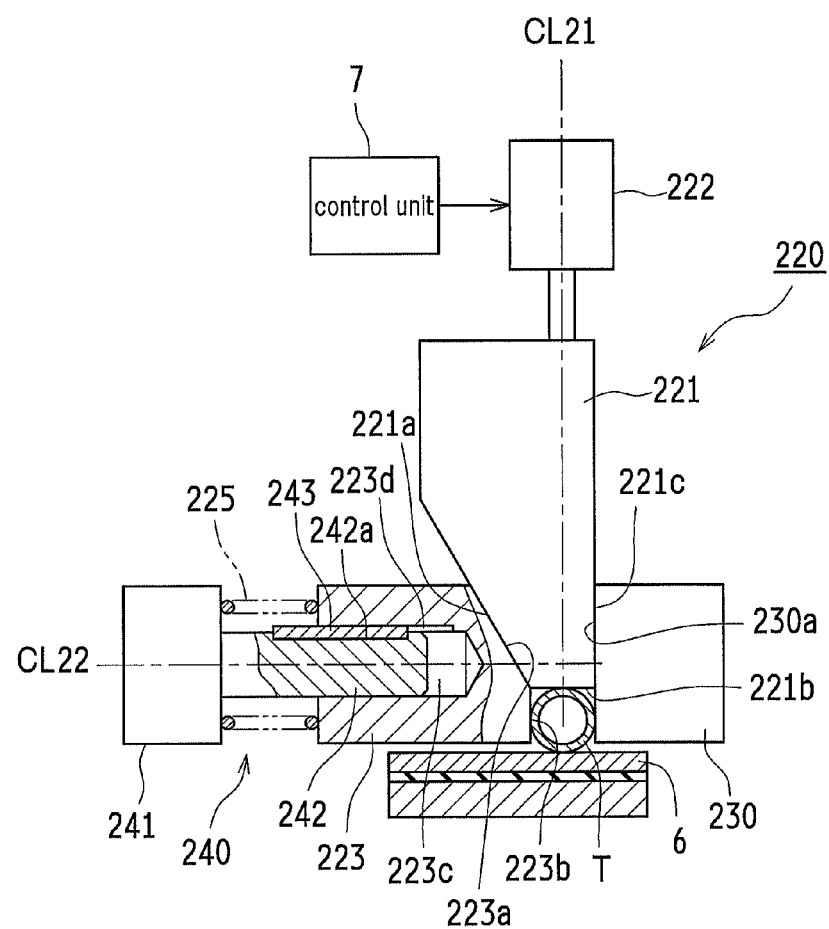
FIG. 12 A diagram illustrating a configuration of principal portions of the other example of the infusion pump according to the present invention.

Further, the structure which allows the secondary finger 223 to slide relative to the pump body 11 (slide in the direction along the central axis CL2 is not limited to that of FIG. 12 and other structures may be employed. For example, a structure in which a guide rod 242 is spline machined, or a structure in which the secondary finger 223 is slidably supported on the pump body 11 by use of the connecting mechanism shown in FIG. 11 (the connecting mechanism in which the T-shaped groove and the T-shaped slider are combined and the connecting mechanism in which the trapezoidal-shaped groove and the trapezoidal-shaped slider are combined) may be involved.

Note that, although in this example the half-occlusion type infusion pump is described to which the present invention is applied, the present invention is not limited thereto, and the full-press type infusion pump whose infusion tube T is fully occluded by the primary finger 221 can be applied.

Embodiment 3

The still other example of the infusion pump according to the present invention will be described with reference to FIGS. 15-23. Note that, in FIGS. 17 and 19-21, an eccentric cam 322a is illustrated without being cut away.

An infusion pump 300 in this example comprises the pump body 11 and the door 12 which closes the front side (at the tube mounting position) of the pump body 11. The door 12 is swingably (turnably) supported on the pump body 11 by the hinges 13, 13 and is adapted to be able to swing from the position to fully close the front side of the pump body 11 to its full open position (for example, the position in which the door is opened at 180 degrees).

In the infusion pump 300 in this example, the configuration other than those described below is essentially same as that of the above [Embodiment 1], and accordingly will not be described in detail.

The infusion pump 300 in this example, which is of a peristaltic finger type (the full-press), comprises a pump mechanism 302

The pump mechanism 302 comprises a plurality of primary fingers 321 . . . 321 arranged along a single direction (a direction along the infusion tube T mounted on the pump body 11) (7 fingers in the example shown in FIG. 17), a plurality of eccentric cams 322a . . . 322a for respectively driving each of the primary fingers 321 . . . 321 to advance and restrict, a cam shaft 322 which rotates each of the eccentric cam 322a, a plurality of secondary fingers 323 . . . 323 provided for each of the primary finger 321 . . . 321, a tube pressing plate 330, a holding frame 340, a guide member 341, etc.

The primary fingers 321 . . . 321 and the secondary fingers 323 . . . 323 of the pump mechanism 302 are adjacent to the front side of the pump body 11 via an opening 110d of the front wall 110 of the pump body 11. Also the door 12 is provided with the tube pressing plate 330. The tube pressing plate 330 is provided in a position corresponding to the pump mechanism 302 (the primary fingers 321 . . . 321, etc.). The tube pressing plate 330 is adapted to be opposed to the tip of the primary finger 321 of the pump mechanism 302 (the primary finger 321 in its most retracted position) with a predetermined gap (a gap corresponding to the outer diameter of the infusion tube T) when the door 12 is closed.

The primary fingers 321 . . . 321 are plate-like members and can be advanced and retracted (move forward and backward) individually in the front-rear direction of the pump body 11 (the direction orthogonal to the longitudinal direction of the infusion tube T mounted on the pump body 11, i.e., the direction orthogonal to the front wall 110 of the pump body 11).

The primary fingers 321 . . . 321 are held on the holding frame 340. The front side of the holding plate 340 has openings 340a . . . 340a which are respectively provided in the position corresponding to each of the primary fingers 321 . . . 321. Each tip portion of the primary fingers 321 . . . 321 is adjacent to the front side (the infusion tube T side) of the holding frame 340 via the respective opening 340a. In addition, the guide member 341 is mounted to the rear side of the holding frame 340, and the guide member 341 and walls between the openings 340a of the holding frame 340 restricts the movement of the primary fingers 321 . . . 321 in their axial direction (an axial direction of the cam shaft 322).

Each of the primary fingers 321 has the respective cam hole 321c formed therein. The disk-like eccentric cam 322a is respectively fitted into each of the cam hole 321c. Each of the eccentric cams 322a is rotable within the respective cam hole 321c, and these eccentric cams 322a . . . 322a are attached to the cam shaft 322 to be integrally rotatable.

Figure 19:
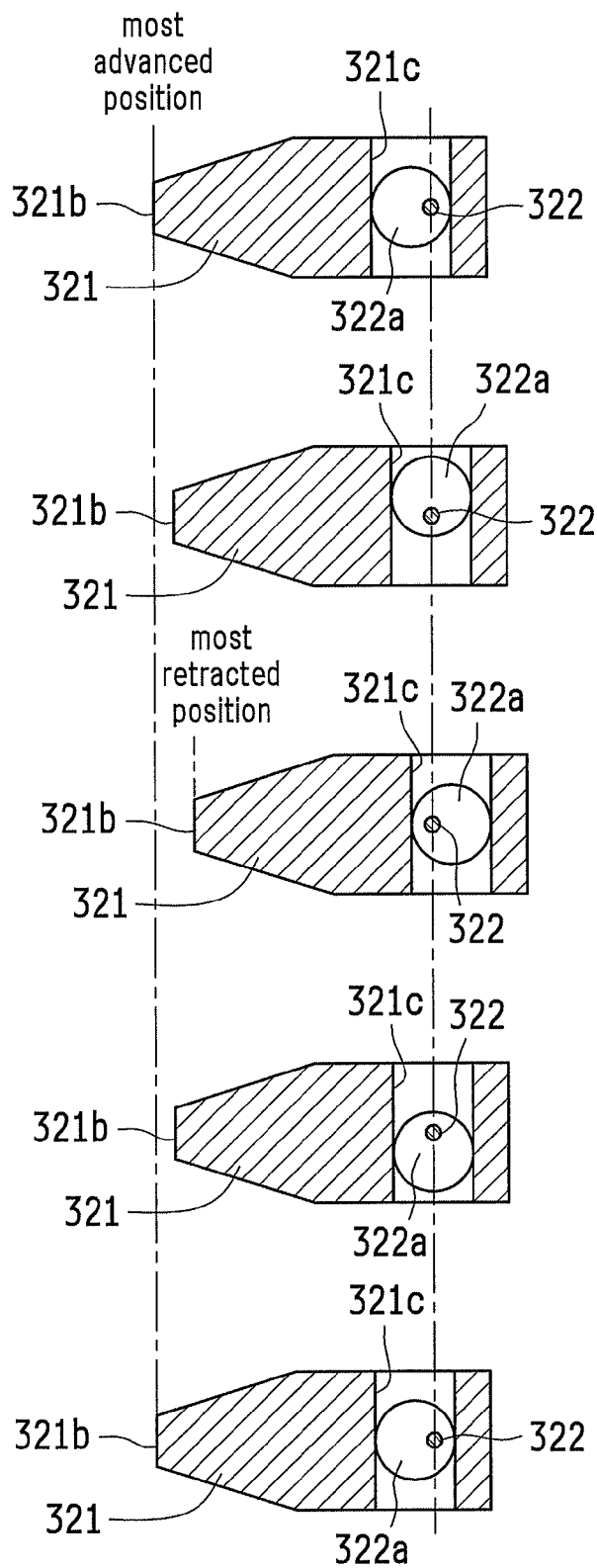
FIG. 19 Operation illustrations of the primary fingers of the infusion pump in FIG. 15 in a cross sectional view, in which each of the primary fingers is taken along a surface orthogonal to the cam shaft.
Figure 20:
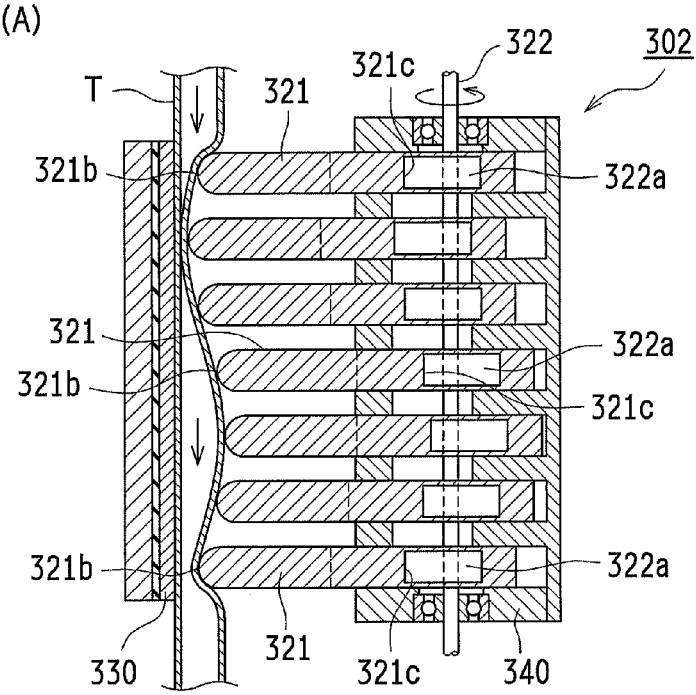
FIG. 20 Operation explanatory diagrams of the pump mechanism illustrated in FIG. 17.
Figure 20:
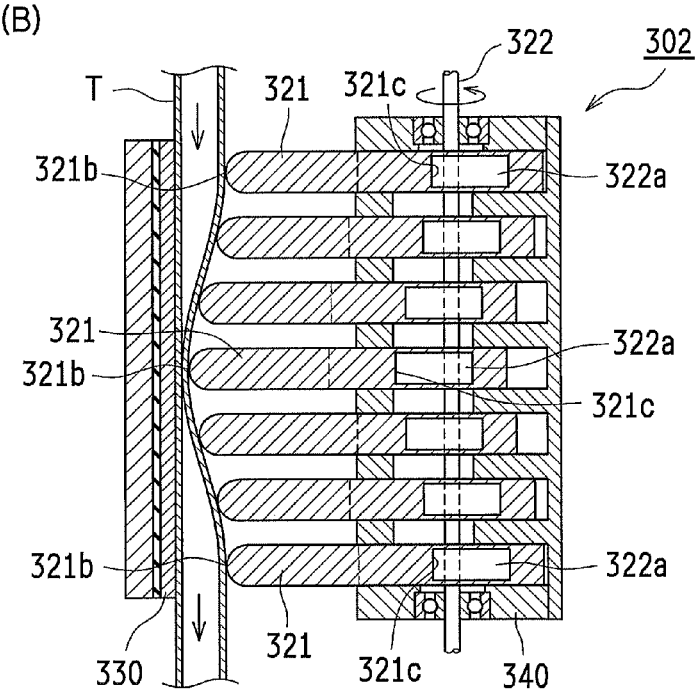
Figure 21:
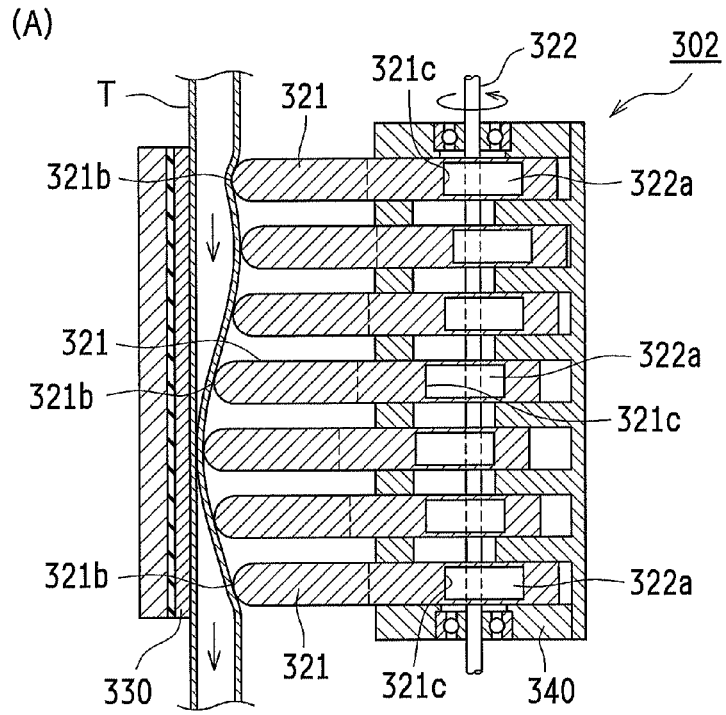
FIG. 21 Operation explanatory diagrams of the pump mechanism illustrated in FIG. 17.
Figure 21:
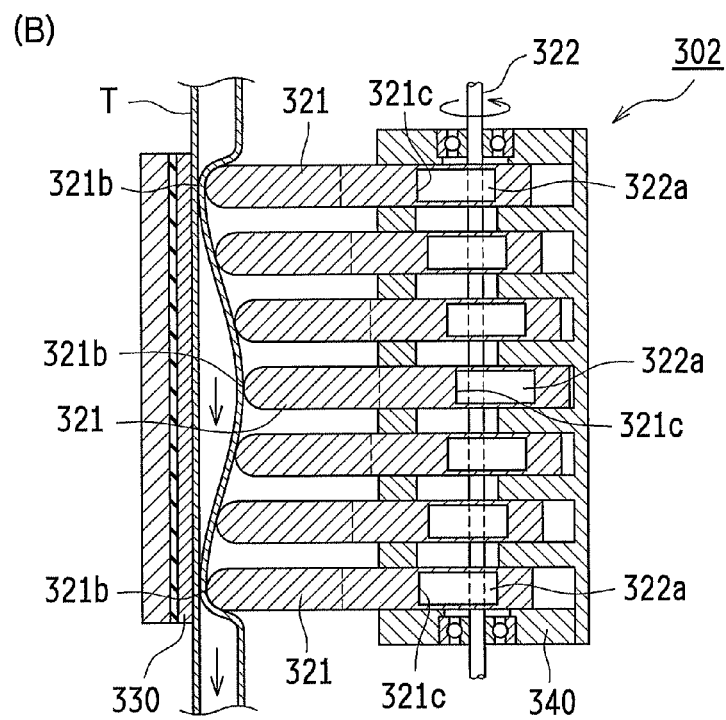

The center of each of the disk-like eccentric cams 322a is eccentric with respect to the cam shaft 322, and as shown in FIG. 19, during the cam shaft 322 is rotated by one rotation (rotated through 360°), a tip 321b of the primary finger 321 would undergo a single stroke between its most advanced position (tube occluding position) and its most retracted position (tube full-open position). In addition the plurality of the eccentric cams 322a . . . 322a are attached to the cam shaft 322 with a predetermined phase difference with one another (the phase difference in therotational direction of the cam shaft 322). In particular, the eccentric cams 322a . . . 322a are attached to the cam shaft 322 with the phase difference (360°/a number of the eccentric cams 322a) such that the tips 321b . . . 321b of the primary fingers 321 . . . 321 aligned in an axial direction of the cam shaft 322 conform with the substantially sinusoidal wave. Note that FIG. 19 shows the positions of the primary finger 321 for every 90° rotation of the cam shaft 322.

Figure 17:
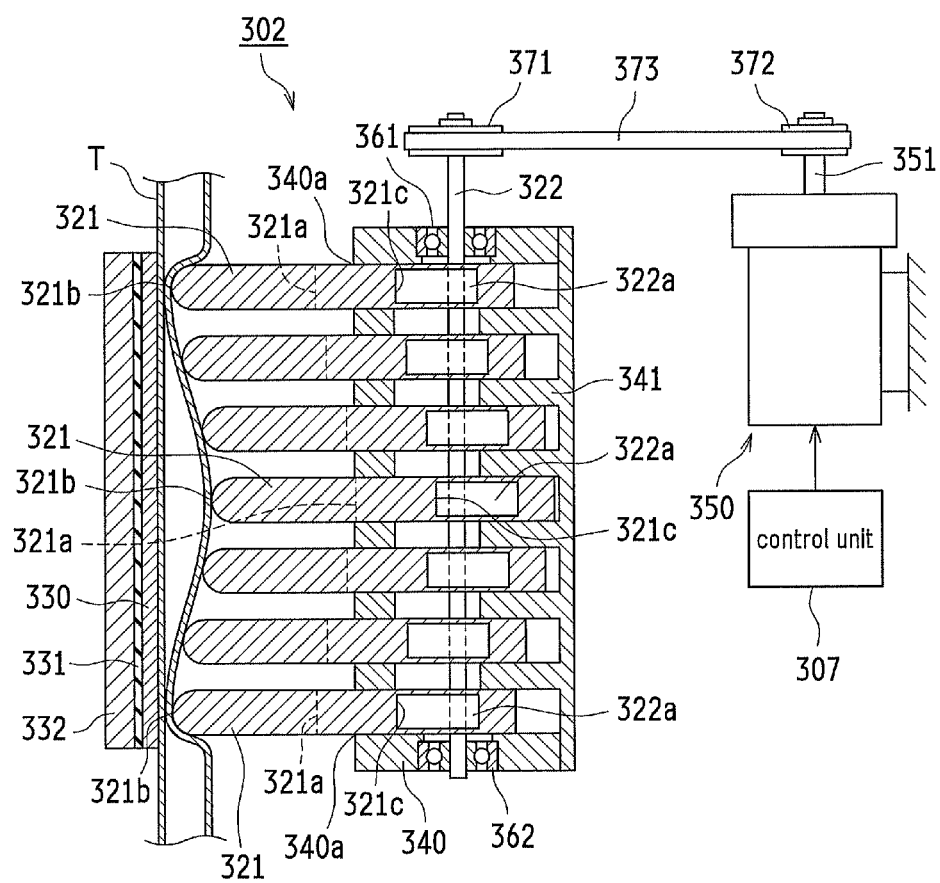
FIG. 17 A cross sectional view of a configuration of the pump mechanism applied to the infusion pump in FIG. 15, which is cut along a surface along a cam shaft of the pump mechanism.

The cam shaft 322 of the pump mechanism 302 described above is provided along the vertical direction (an arranging direction of the plurality of the primary fingers 321 . . . 321) as shown in FIG. 17.

A lower end of the cam shaft 322 is rotatably supported by a bearing 362 provided on the holding frame 340. An upper portion of the cam shaft 322 is projected upward through the wall of the holding frame 340. The projected portion of the cam shaft 322 has a bearing 361 by which the upper portion of the cam shaft 322 is rotatably supported.

A timing pulley (idler pulley) 371 is attached to an upper end of the cam shaft 322 to integrally rotatable. A timing belt 373 is wounded between the timing pulley 371 of the cam shaft 322 and another timing pulley (driving pulley) 372 attached to the rotational shaft 351 of an electric motor (for example, stepping motor) 350 to be integrally rotatable, so that driving the electric motor 350 causes the cam shaft 322 to be rotated. The electric motor 350 is drive-controlled (rotation-controlled) by the control unit 307. Note that, in this example, the electric motor 350 is powered from any battery contained in the infusion pump 1 or any commercial power source.

Further, when driving the electric motor 350 causes the cam shaft 322 to rotate, each of the eccentric cam 322a is rotated within the cam hole 321c of the primary finger 321. As each of the eccentric cam 322a is eccentrically rotated, each of the primary finger 321 is sequentially advanced and retracted from the upstream side (the upstream side in the infusion delivery direction) to the downstream side. In particular, as shown in FIGS. 20(A), (B) and 21(A), (B), the tips 321b of the primary fingers 321 move from the upstream side to the downstream side in a peristaltic wave manner. Through the advancing and retracting (stroke movement) of the primary fingers 321 . . . 321 in this way, the peristaltic motion is imparted to the infusion tube T positioned between these tips 321b . . . 321b of the primary fingers 321 . . . 321 and the tube pressing plate 330, so that the infusion solution within the infusion tube T is sent out from the upstream side to the downstream side. Note that, in this example, in order to mitigate the overload on the infusion tube T by the primary fingers 321 . . . 321, a buffer sheet 331 is provided between the tube pressing plate 330 and a base plate 332.

—Control Unit—

A control unit 307 is constituted mainly by a microcomputer etc. The control unit 307 is connected to, but not illustrated, an air bubble sensor (e.g., an ultrasonic sensor) which detects air bubbles mixed into the infusion tube T mounted on the pump body 11, an open/close sensor which detects a closed state of the door 12, a distance sensor, etc. as described later and output signals from each sensor are input to the control unit 307.

The control unit 307 regulates variably the rate of infusion by controlling a number of rotation of the electric motor 350 in a pump driving mechanism 302 in accordance with the set value for the rate of infusion (the delivery amount of infusion per unit time) which is set (input) through the operation of the operation panel 122 on the display operation unit 120 (see, FIG. 1). In this example, the rate of infusion may be set every [1 mL/h] between 1 mL/h-1200 mL/h, for example.

In addition, the control unit 307 is configured to display, on the display panel 121 (see FIG. 1) of the display operation unit 120, the operation information such as "a rate of infusion (infusion amount)" and "an accumulated infusion time" and to display various alerts including such as "Air Bubbles Containing Fault" and "Door Open" as well as to operate an alarm buzzer device.

—Technical Feature—

We will explain the technical features of the infusion pump 300 in this example.

The infusion pump 300 in this example has a pair of secondary fingers 223, 223 positioned on the right and left sides of the primary finger 321. Note that, since the plurality of primary fingers 321 . . . 321 and the plurality pairs of secondary fingers 323, 323 provided for each of the primary fingers 321 have the same configuration, a single primary finger 321 and a pair of secondary fingers 323, 323 will be described below.

A pair of inclined surfaces 321a, 321a are provided on the right and left side surfaces of the primary finger 321. The pair of inclined surfaces 321a, 321a is opposingly inclined in an advancing and retracting direction of the primary finger 321 (a central axis CL 31 direction) and tapered so as that the distance between the inclined surfaces 321a, 321a is decreasing toward the tip of the primary finger 321. The angle of inclination for the inclined surfaces 321a, 321a (the angle of inclination to a central axis CL31) is the same value as in the above-described [Embodiment 1] ("15.9°" or "16°±β").

A central axis CL31 of the primary finger 321 is positioned along the front-rear direction of the pump body 11 (the direction orthogonal to the longitudinal direction of the infusion tube T mounted on the pump body 11, i.e., the direction orthogonal to the front wall 110 of the pump body 11).

Figure 18:
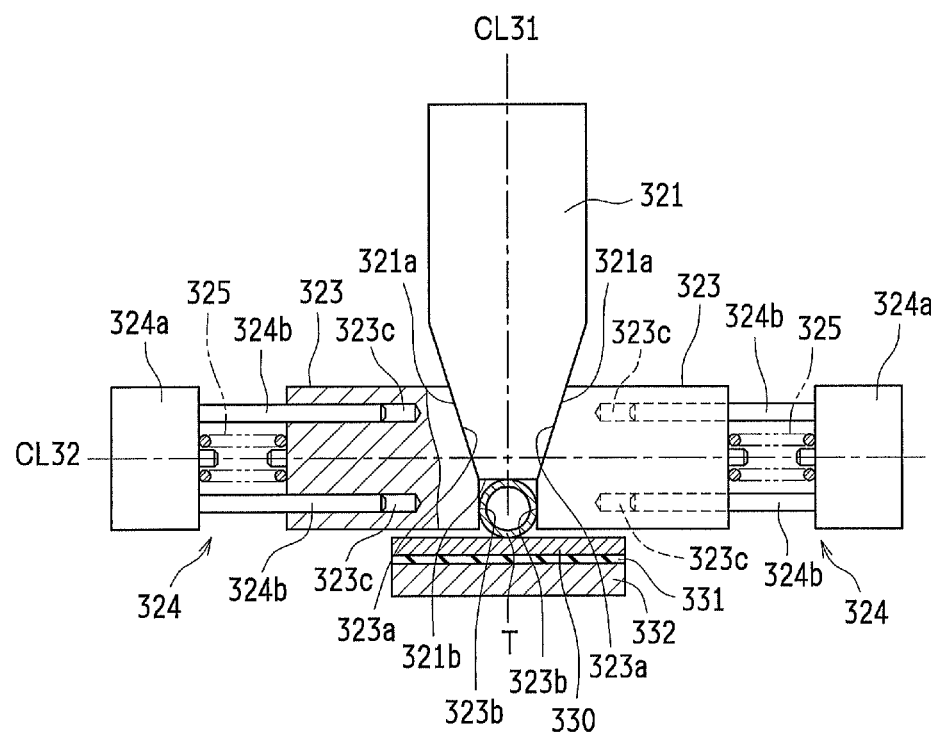
FIG. 18 A partially cut-away view from Y direction of FIG. 16.

The primary finger 321 is advanced and retracted (moves forward and backward) by rotating the eccentric cam 322a as described above, and when the primary finger 321 in its most retracted position the tip 321b of the primary finger 321 is placed in the position in contact with the outer peripheral surface of the infusion tube T (in the perfect circle) mounted on the pump body 11 (i.e., in the position corresponding to the outer peripheral surface of the infusion tube T) as shown in FIGS. 18 and 22(A) etc. Furthermore, when the primary finger 321 is advanced from this state (in its most retracted position), the infusion tube T is pressed in the advancing process. Here, since the infusion pump 1 in this example is of the full-press type, when the primary finger 321 is in its most advanced position, the infusion tube T is fully occluded in its most advanced position as shown in FIG. 22(C).

The pair of secondary fingers 323, 323 is positioned on the both sides of the primary finger 321. The pair of secondary fingers 323, 323 with the same shape and dimension is positioned bilaterally symmetrically. The secondary fingers 323, 323 each are plate-like members and have the respective inclined surfaces 323a, 323a at their tip portions (on their primary finger 321 side) which slide relative to the inclined surfaces 321a, 321a of the primary finger 321. The angle of inclination for the inclined surfaces 323a, 323a of the secondary finger 323 (the angle of inclination to the central axis CL31 of the primary finger 321) is the same value as in the above-described [Embodiment 1] ("15.9°" or "16°±β").

The central axis CL32 of the secondary fingers 323, 323 is placed in the direction orthogonal to the central axis CL31 of the primary finger 321 (the direction parallel to the front wall of the pump body 11). Further, each of secondary fingers 323, 323 has also two guide through holes 323c, 323c parallel to the central axis CL32. The two guide through holes 323c, 323c are positioned vertically to sandwich the central axis CL32 of the secondary finger 323 between them. The inner diameter of each of the guide through holes 323c is set larger than the outer diameter of a guide rod 324b described below by a predetermined amount so that the secondary finger 323 is adapted to be slidable relative to the guide rod 324b.

The secondary fingers 323, 323 are slidably supported by the sliding support member 324, 324. Each of the sliding support members 324, 324 has a base member 324a and the two guide rods 324b, 324b, which are integrally provided thereon. The central axis of the each guide rod 342b is along the direction parallel to the central axis CL32. The base members 241, 241 are supported and fixed on the pump body 11.

The two guide rods 324b, 324b of the each sliding support member 324 are positioned vertically to sandwich the central axis CL32 of the secondary finger 323 between them. This results that the movement (rotation) of the secondary fingers 323, 323 about the central axis CL32 is restricted and the secondary fingers 323, 323 are adapted to be slidable (advance and retreat) in the axial direction of the guide rods 324b, 324b, in other words, in one direction orthogonal to the advancing and retracting direction of the primary finger 321.

In addition, compression coil springs (resilient members) 325, 325 are sandwiched between the rear end surfaces of the secondary fingers 323, 323 and the base members 324a, 324a, and the resilient force of the compression coil springs 325, 325 presses the secondary fingers 323, 323 toward the primary finger 321, so that the inclined surfaces 323a, 323a of the secondary fingers 323, 323 are pressed and abut on the inclined surfaces 321a, 321a of the primary finger 321, respectively.

Thus, pressing the secondary fingers 323, 323 by the compression coil springs 325, 325 in this way causes that in the process in which the primary finger 321 is advanced and retracted between its most retracted position and its most advanced position, the inclined surfaces 321a, 321a of the primary finger 321 and the inclined surfaces 323a, 323a of the secondary fingers 323, 323 slide in contact with each other, and the secondary fingers 323, 323 are moved in conjunction with the primary finger 321 being advanced and retracted because the inclined surfaces 323a, 323a of the secondary fingers 323, 323 are not separated from the inclined surfaces 321a, 321a of the primary finger 321.

In particular, when the primary finger 321 is advanced, the inclined surfaces 321a, 321a of the primary finger 321 and the inclined surfaces 323a, 323a of the secondary fingers 323, 323 slide relative to each other, and each of the secondary finger 323, 323 is retracted in conjunction with the movement of the primary finger 321 (the pair of the secondary finger 323, 323 apart from each other). On the other hand, when the primary finger 321 is retracted, the resilient force of the compression coil spring 325 causes the inclined surfaces 321a, 321a of the primary finger 321 and the inclined surfaces 323a, 323a of the secondary fingers 323, 323 to slide relative to each other and each of the secondary fingers 323, 323 is advanced in conjunction with the movement of the primary finger 321 (the pair of secondary fingers 323, 323 is move in the direction to be close to with each other).

—Operation Explanation of Primary Finger and Secondary Finger—

Figure 22:
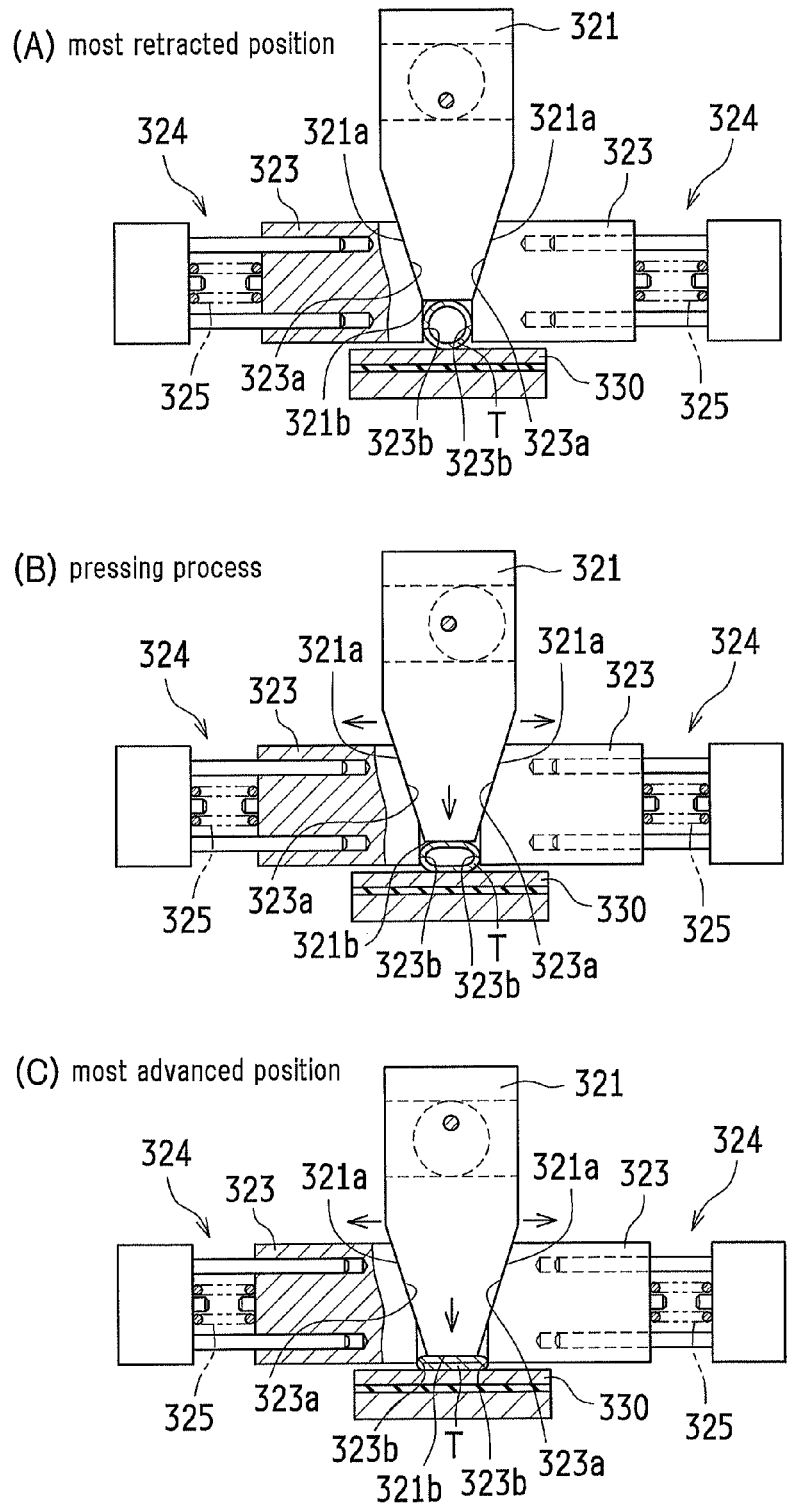
FIG. 22 Operation explanatory diagrams of the primary finger and the secondary fingers of the tube pressing section illustrated in FIG. 18.
Figure 23:
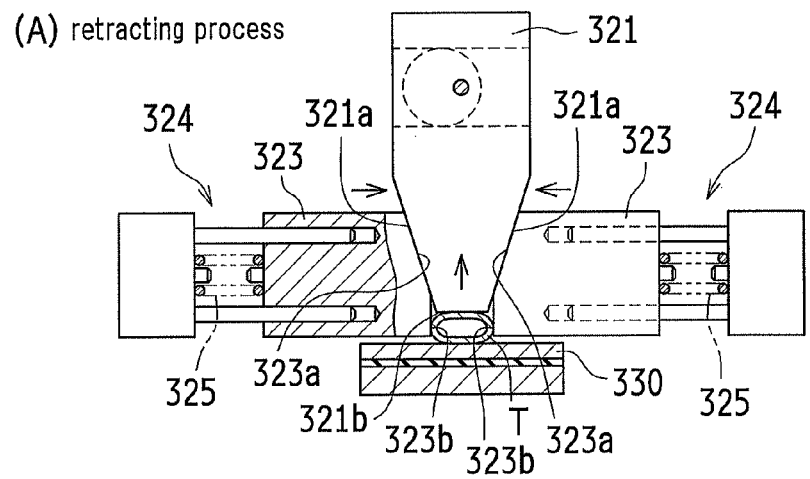
FIG. 23 Operation explanatory diagrams of the primary finger and the secondary fingers of the tube pressing section illustrated in FIG. 18.
Figure 23:
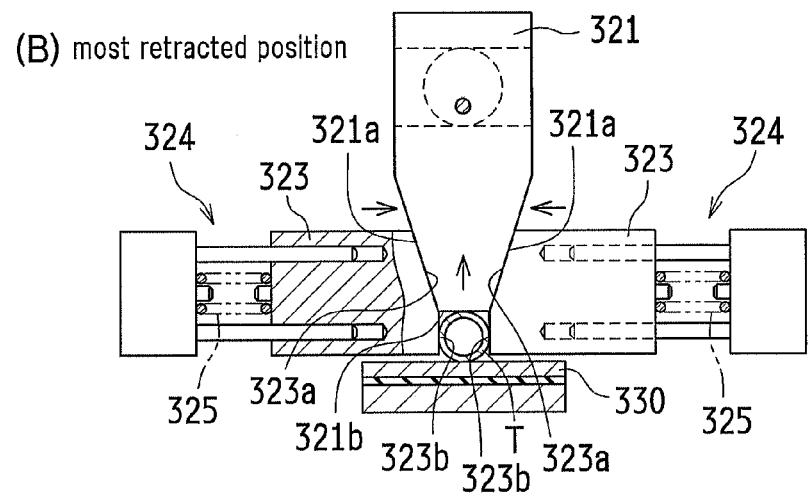
Figure 24:
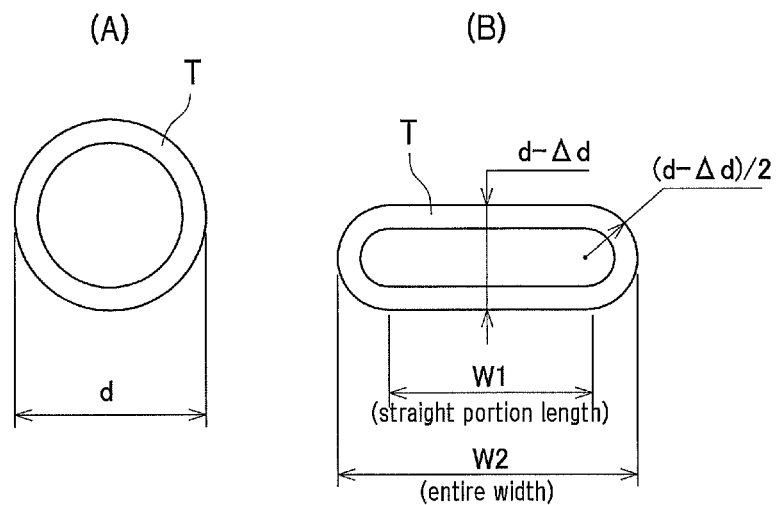
FIG. 24 A diagram illustrating a relationship between an amount of compression Δd and an entire width W2.

Next, the operation of the primary finger 321 and the pair of secondary fingers 323, 323 will be described with reference to FIGS. 22 and 23.

[S31] Firstly, as shown in FIG. 22(A), when the primary finger 321 is in its most retracted position (initial position), the tip 321b of the primary finger 321 and the tip surfaces 323b, 323b of the pair of secondary fingers 323, 323 are positioned on the outer peripheral surface of the infusion tube T (in a position corresponding to the outer peripheral surface). Also the tube pressing plate 330 is in contact with the outer peripheral surface of the infusion tube T.

[S32] From the state shown in FIG. 22(A), when the primary finger 321 is advanced, the tip 321b of the primary finger 321 presses the infusion tube T, so that the infusion tube T is compressed (FIG. 22(B)). Moreover, in the advancing process of the primary finger 321, the sliding of the inclined surfaces 321a, 321a of the primary finger 321 and each of the inclined surfaces 323a, 323a of the secondary fingers 323, 323 relative to each other causes the pair of secondary fingers 323, 323 to be moved (retracted) against the resilient force of the compression coil spring 325, 325 in the direction orthogonal to the tube pressing direction (along to the central axis CL32 shown in FIG. 18). At this time, since the pair of secondary fingers 323, 323 is moved in proportion to the variation (increasing) in the entire width of the infusion tube T deformed due to advancing the primary finger 321 (the entire width shown in FIG. 26: $(\pi/2-1)\Delta d+d$)), in the advancing process of the primary finger 321, the tip surfaces 323b, 323b of the secondary fingers 323, 323 are always placed in the position corresponding the outer peripheral surface (side surface) of the infusion tube T.

[S33] From the state shown in FIG. 22(B), when the primary finger 321 is further advanced to reach its most advanced position, the infusion tube T is further pressed into the state shown in FIG. 22(C). That is to say, the infusion tube T is occluded by the primary finger 321. Also, since the pair of secondary fingers 323, 323 is moved (retracted) in proportion to the variation (increasing) in the entire width of the infusion tube T in this movement process of the primary finger 321 to its most advanced position, each of the tip surfaces 323b, 323b of the secondary fingers 323, 323 is placed in the position corresponding to the outer peripheral surface (side surface) of the compressed infusion tube T, with the primary finger 321 reaching its most advanced position.

[S34] From the state shown in FIG. 22(C) (in the most advanced position), when the primary finger 321 is moved (retracted) in an opposite direction to that in pressing the primary finger 321, the compressed infusion tube T is restored in the original shape due to the tube's own restoring force (resilient force) along with the retracting of the primary finger 321 (FIG. 23(A)).

Here, since the inclined surfaces 323a, 323a of the secondary fingers 323, 323 are pressed against the inclined surfaces 221a, 221a of the primary finger 321 due to the resilient force of the compression coil spring 325, and remains to slide relative to the inclined surfaces 21a, 21a of the primary finger 321, when the primary finger 321 is retracted, the pair of secondary fingers 323, 323 is moved (advanced) due to the resilient force of the compression coil springs 325, 325. At this time, since the pair of secondary fingers 323, 323 is advanced in proportion to the variation (decreasing) in the entire width of the infusion tube T deformed (restored) due to retracting the primary finger 321 (the entire width shown in FIG. 26: $(\pi/2-1)\Delta d+d$), in the retracting process of the primary finger 321, the tip surfaces 323b, 323b of the secondary fingers 323, 323 are always placed in the position corresponding to the outer peripheral surface (side surface) of the infusion tube T in the restoring process. Accordingly, even when the infusion tube T is not well restored since the side surface of the infusion tube T is pressed by the secondary fingers 323, 323, the infusion tube T would be restored.

[S35] From the state shown in FIG. 23(A), when the primary finger 321 is further retracted to reach its most retracted position, the state shown in FIG. 23(B) is achieved. That is to say, the infusion tube T is fully restored into the original shape (into the substantially perfect circular shape). Also in this movement process of the primary finger 321 to its most retracted position, since the pair of secondary fingers 323, 323 is moved in proportion to the variation (decreasing) in the entire width of the infusion tube T, the tip surfaces 323b, 323b of the secondary fingers 323, 323 are placed in the position corresponding to the outer peripheral surface (side surface) of the restored infusion tube T, with the primary finger 321 reaching its most retracted position. Accordingly, even when the infusion tube T is not well restored since the side surface of the infusion tube T is forcedly pressed by the secondary fingers 323, 323, the infusion tube T can be restored into the substantially perfect circular shape.

As described above, according to the infusion pump 300 in this example, in the advancing and retracting process of the primary finger 321, since the pair of secondary fingers 323, 323 is moved in proportion to the variation in the entire width of the infusion tube T, the occurrence of any gap between each of the tip surfaces 323b, 323b of the secondary fingers 323, 323 and the outer peripheral surface of the infusion tube T can be suppressed. This can prevent the infusion tube T from meandering between the tip 321b of the primary finger 321 and the tube pressing plate 6 of even the infusion pump 300 is of the full-press type, and the accuracy of the rate of infusion can be improved.

Moreover, since the sliding of the primary finger 321 and the secondary fingers 323, 323 causes the secondary fingers 23, 23 to move, only one single driving system is required for the fingers (only one system is required for the primary finger 321) and the reduction in cost can be contemplated. Also, it is advantageously in that the phase shift between the movement of the primary finger 321 and the movement of the secondary fingers 323, 323 is not likely to occur comparing to the conventional driving method described above, i.e., the method wherein the primary finger and the secondary finger are driven individually or the method wherein each of the primary finger and the secondary fingers is driven by the respective cam shaft.

Figure 16:
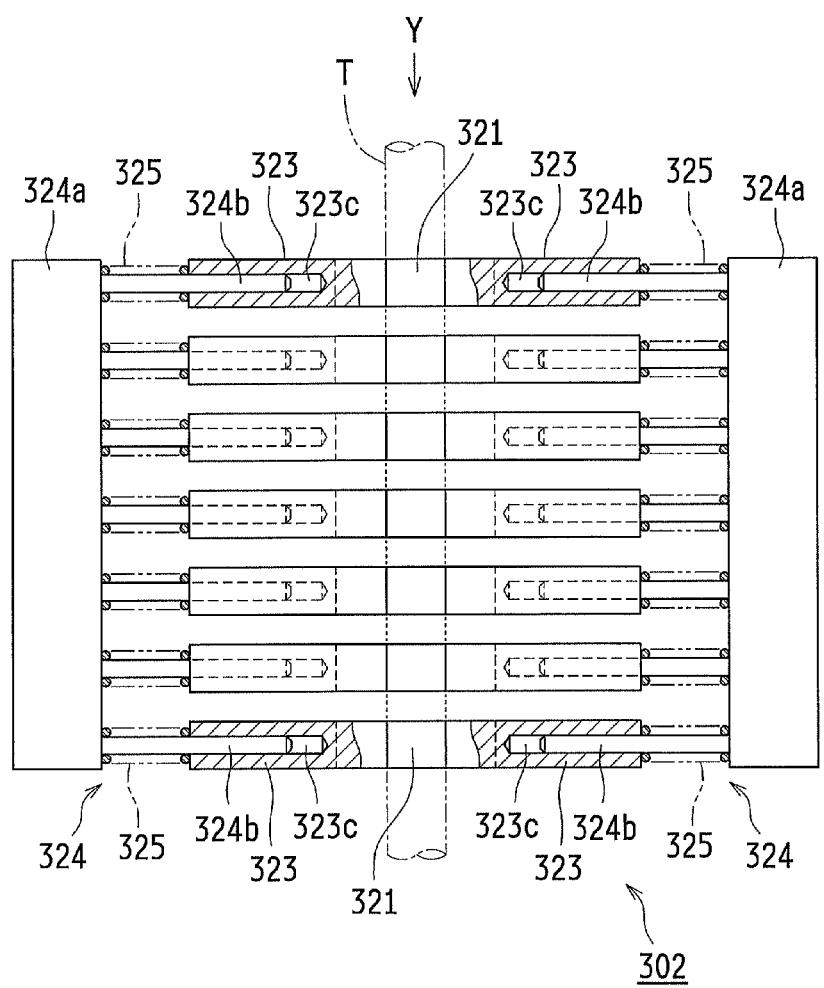
FIG. 16 A partially cut-away front view of a pump mechanism applied to the infusion pump in FIG. 15.

Note that, in the example discussed above, any guide member may be provided in order to avoid the positional shift between the primary finger 321 and each of the secondary fingers 323, 323, i.e., the positional shift in the longitudinal direction of the infusion tube T mounted on the pump body 11 (the positional shift in the vertical direction in FIG. 16).

Here, in the above example, although the plurality of primary fingers 321 are provided so as to be separated with each other, the plurality of the primary fingers 321 may be positioned in contact with each other (in a slidable state).

Moreover, in the above example, although the infusion pump has 7 primary fingers 321, the present invention is not limited thereto, and any other number of primary fingers may be possible, wherein the number is more than one.

Further, in the above example, although two secondary fingers 323, 323 are provided for the single primary finger 321, the present invention is not limited thereto, and a single secondary finger 323 may be provided for the single primary finger 321.

INDUSTRIAL APPLICABILITY

The present invention can be utilized in an infusion pump used such as in the case of infusing an amount of drug solution for medical use into a human body.

EXPLANATION OF REFERENCES 1, 300: infusion pump
11: pump body
12: door
2, 302: pump mechanism
20, 220: tube pressing section
21, 221, 321: primary finger
21a, 221a, 321a: inclined surface (sliding surface)
22, 222: actuator
23, 223, 323: secondary finger
23a, 223a, 323a: inclined surface (sliding surface)
25, 225, 325: compression coil spring (resilient member)
30: upstream side valve section
31: upstream side valve finger
40: downstream side valve section
41: downstream side valve finger
6, 330: tube pressing plate
7, 307: control unit
350: electric motor
T: infusion tube

The invention claimed is:

1. An infusion pump comprising a pump mechanism which presses an infusion tube to deliver an amount of infusion solution within the infusion tube,
wherein the pump mechanism comprises:
a primary finger capable of being advanced and retracted in an advancing and retracting direction relative to the infusion tube, the primary finger having a pair of tapered inclined surfaces opposingly inclined to the advancing and retracting direction, and the primary finger pressing the infusion tube when the primary finger is advanced;
driving means which moves the primary finger in the advancing and retracting direction; and
a pair of secondary fingers each capable of being advanced and retracted only in one direction orthogonal to the advancing and retracting direction of the primary finger, each of the pair of secondary fingers having an inclined surface arranged to contact and slidable relative to one of the tapered inclined surfaces of the primary finger,
wherein when the primary finger is advanced and retracted, the tapered inclined surfaces of the primary finger and the inclined surfaces of the secondary fingers are arranged to slide in contact with each other, thereby causing the secondary fingers to move in conjunction with the movement of the primary finger in the directions orthogonal to the advancing and retracting direction of the primary finger,
wherein, when the primary finger is advanced, the secondary fingers are retracted in proportion to a variation in an entire width of the infusion tube, and when the primary finger is retracted, the secondary fingers are advanced in proportion to the variation in the entire width of the infusion tube, and
wherein, with an angle of inclination for the tapered inclined surfaces of the primary finger relative to a central axis being $\theta 1$, $\theta 1$ is set to satisfy $\theta 1 = \tan^{-1}(\pi/4 - 1/2)$.

2. The infusion pump according to claim 1, further comprising
a resilient member which presses the inclined surfaces of the secondary fingers against the tapered inclined surfaces of the primary finger, wherein the tapered inclined surfaces of the primary finger and the inclined surfaces of the secondary fingers are configured to slide relative to each other due to a resilient force of the resilient member when the primary finger is retracted.

3. The infusion pump according to claim 1, further comprising
connecting means which slidably connects the primary finger and the secondary fingers,
wherein the tapered inclined surfaces of the primary finger and the inclined surfaces of the secondary fingers are configured to slide relative to each other due to the connection of the connecting means when the primary finger is retracted.

4. The infusion pump according to claim 1,
wherein the pump mechanism further comprises an upstream side valve finger which occludes openably/closably the infusion tube on an upstream side of an infusion delivery direction of the primary finger, and a downstream side valve finger which occludes openably/closably the infusion tube on a downstream side of an infusion delivery direction of the primary finger.

5. The infusion pump according to claim 1,
wherein the primary finger is a plurality of primary fingers capable of being advanced and retracted relative to the infusion tube, the plurality of primary fingers pressing the infusion tube when the plurality of primary fingers is advanced, and
wherein the driving means individually moves the plurality of primary fingers in the advancing and retracting direction, the amount of infusion solution being sent out in a peristaltic motion by driving each of the plurality of primary fingers to advance and retract to the infusion tube, wherein the pair of secondary fingers is a plurality of secondary fingers provided for the primary fingers of the pump mechanism.

6. An infusion pump comprising a pump mechanism which presses an infusion tube to deliver an amount of infusion solution within the infusion tube,
wherein the pump mechanism comprises:
a primary finger capable of being advanced and retracted relative to the infusion tube, the primary finger pressing the infusion tube when the primary finger is advanced;
driving means which moves the primary finger in the advancing and retracting direction; and
a secondary finger capable of being advanced and retracted only in one direction orthogonal to the advancing and retracting direction of the primary finger,
wherein the primary finger has an inclined surface which is obliquely inclined to the advancing and retracting direction, and the secondary finger has an inclined surface which is arranged to contact the inclined surface of the primary finger,
wherein when the primary finger is advanced and retracted, the inclined surface of the primary finger and the inclined surface of the secondary finger are arranged to slide in contact with each other, thereby causing the secondary finger to move in conjunction with the movement of the primary finger in the direction orthogonal to the advancing and retracting direction of the primary finger,
wherein, when the primary finger is advanced, the secondary finger is retracted in proportion to a variation in an entire width of the infusion tube, and when the primary finger is retracted, the secondary finger is advanced in proportion to the variation in the entire width of the infusion tube,
wherein the inclined surface of the primary finger is an inclined surface inclined to the advancing and retracting direction, and the secondary finger is a single secondary finger with an inclined surface slidable relative to the inclined surface of the primary finger, and
wherein, with an angle of inclination for the inclined surface of the primary finger relative to a central axis being $\theta 2$, $\theta 2$ is set to satisfy $\theta 2 = \tan^{-1}(\pi/2 - 1)$.

7. The infusion pump according to claim 6, further comprising
a resilient member which presses the inclined surface of the secondary finger against the inclined surface of the primary finger, wherein the inclined surface of the primary finger and the inclined surface of the secondary finger are configured to slide relative to each other due to a resilient force of the resilient member when the primary finger is retracted.

8. The infusion pump according to claim 6, further comprising
connecting means which slidably connects the primary finger and the secondary finger,
wherein the inclined surface of the primary finger and the inclined surface of the secondary finger are configured to slide relative to each other due to the connection of the connecting means when the primary finger is retracted.

9. The infusion pump according to claim 6,
wherein the pump mechanism further comprises an upstream side valve finger which occludes openably/closably the infusion tube on an upstream side of an infusion delivery direction of the primary finger, and a downstream side valve finger which occludes openably/closably the infusion tube on a downstream side of an infusion delivery direction of the primary finger.

10. The infusion pump according to claim 6,
wherein the primary finger is a plurality of primary fingers capable of being advanced and retracted relative to the infusion tube, the plurality of primary fingers pressing the infusion tube when the plurality of primary fingers is advanced, and
wherein the driving means individually moves the plurality of primary fingers in the advancing and retracting direction, the amount of infusion solution being sent out in a peristaltic motion by driving each of the plurality of primary fingers to advance and retract to the infusion tube, wherein the secondary finger is a plurality of secondary fingers provided for the primary fingers of the pump mechanism.

* * * * *